(12) United States Patent
Power et al.

(10) Patent No.: US 7,600,511 B2
(45) Date of Patent: Oct. 13, 2009

(54) APPARATUS AND METHODS FOR DELIVERY OF MEDICAMENT TO A RESPIRATORY SYSTEM

(75) Inventors: John Power, Galway (IE); Desmond Regan, County Galway (IE); Declan Moran, County Galway (IE)

(73) Assignee: Novartis Pharma AG, Basel (CH)

( * ) Notice: Subject to any disclaimer, the term of this patent is extended or adjusted under 35 U.S.C. 154(b) by 62 days.

(21) Appl. No.: 10/284,068

(22) Filed: Oct. 30, 2002

(65) Prior Publication Data

US 2003/0150445 A1 Aug. 14, 2003

Related U.S. Application Data

(60) Provisional application No. 60/344,484, filed on Nov. 1, 2001, provisional application No. 60/381,830, filed on May 20, 2002.

(51) Int. Cl.
*A61M 15/00* (2006.01)
*A61M 11/00* (2006.01)

(52) U.S. Cl. .................. 128/200.24; 128/200.14; 128/200.16; 128/200.17; 128/203.12

(58) Field of Classification Search ........... 128/200.14, 128/200.18, 200.19, 200.21, 202.28, 202.29, 128/203.11, 205.15, 200.16, 203.12, 204.14, 128/204.18, 204.24, 204.25, 204.26, 204.27, 128/205.24, 203.15, 203.19, 203.21, 203.24, 128/203.25, 203.29, 203.13, 203.14, 203.16, 128/203.17, 203.22, 203.26, 203.27; 239/4, 239/110, 120–122, 338, 343, 370, 406; 604/83, 604/85, 187, 218; 222/196; 347/54, 68, 347/70

See application file for complete search history.

(56) References Cited

U.S. PATENT DOCUMENTS

| | | | |
|---|---|---|---|
| 550,315 | A | 11/1895 | Allen |
| 809,159 | A | 1/1906 | Willis et al. |
| 1,680,616 | A | 8/1928 | Horst |
| 2,022,520 | A | 11/1935 | Philbrick |
| 2,101,304 | A | 12/1937 | Wright |
| 2,158,615 | A | 5/1939 | Wright |
| 2,187,528 | A | 1/1940 | Wing |
| 2,223,541 | A | 12/1940 | Baker |
| 2,266,706 | A | 12/1941 | Fox et al. |

(Continued)

FOREIGN PATENT DOCUMENTS

| | | |
|---|---|---|
| BE | 531640 | 12/1957 |

(Continued)

OTHER PUBLICATIONS

Fink, James B., "Aerosol Drug Therapy," Clinical Practice in Respiratory Care; Chapter 12, pp. 308-342; 1999.

(Continued)

*Primary Examiner*—Patricia Bianco
*Assistant Examiner*—Keri J Nicholson
(74) *Attorney, Agent, or Firm*—Michael J. Mazza

(57) ABSTRACT

Apparatus and methods are provided for delivery of a medicament to a respiratory system. A reservoir is provided for a liquid medicament with the reservoir having a liquid medicament inlet port and a medicament outlet. An aerosol generator is provided at the medicament outlet of the reservoir for aerosolizing the liquid medicament. A connector entrains the aerosolized medicament from the aerosol generator with a gas.

27 Claims, 26 Drawing Sheets

U.S. PATENT DOCUMENTS

| | | | |
|---|---|---|---|
| 2,283,333 A | 5/1942 | Martin | |
| 2,292,381 A | 8/1942 | Klagges | |
| 2,360,297 A | 10/1944 | Wing | |
| 2,375,770 A | 5/1945 | Dahlberg | |
| 2,383,098 A | 8/1945 | Wheaton | |
| 2,404,063 A | 7/1946 | Healy | |
| 2,430,023 A | 11/1947 | Longmaid | |
| 2,474,996 A | 7/1949 | Wallis | |
| 2,512,004 A | 6/1950 | Wing | |
| 2,521,657 A | 9/1950 | Severy | |
| 2,681,041 A | 6/1954 | Zodtner et al. | |
| 2,705,007 A | 3/1955 | Gerber | |
| 2,735,427 A | 2/1956 | Sullivan | |
| 2,764,946 A | 10/1956 | Henderson | |
| 2,764,979 A | 10/1956 | Henderson | |
| 2,779,623 A | 1/1957 | Eisenkraft | |
| 2,935,970 A | 5/1960 | Morse et al. | |
| 3,066,669 A | 12/1962 | DeMelfy | |
| 3,083,707 A * | 4/1963 | Seeler | 128/200.14 |
| 3,103,310 A | 9/1963 | Lang | |
| 3,247,849 A * | 4/1966 | Wise et al. | 128/200.14 |
| 3,325,031 A | 6/1967 | Singier | |
| 3,411,854 A | 11/1968 | Rosler et al. | |
| 3,515,348 A | 6/1970 | Coffman, Jr. | |
| 3,530,856 A * | 9/1970 | Bird et al. | 128/200.18 |
| 3,550,864 A | 12/1970 | East | |
| 3,558,052 A | 1/1971 | Dunn | |
| 3,561,444 A * | 2/1971 | Boucher | 128/200.16 |
| 3,563,415 A | 2/1971 | Ogle | |
| 3,680,954 A | 8/1972 | Frank | |
| 3,719,328 A | 3/1973 | Hindman | |
| 3,738,574 A | 6/1973 | Guntersdorfer et al. | |
| 3,771,982 A | 11/1973 | Dobo | |
| 3,790,079 A | 2/1974 | Berglund et al. | |
| 3,804,329 A | 4/1974 | Martner | |
| 3,812,854 A | 5/1974 | Michaels et al. | |
| 3,826,413 A | 7/1974 | Warren | |
| 3,838,686 A | 10/1974 | Szekely | |
| 3,842,833 A | 10/1974 | Ogle | |
| 3,858,739 A | 1/1975 | Turner et al. | |
| 3,861,386 A | 1/1975 | Harris et al. | |
| 3,865,106 A | 2/1975 | Palush | |
| 3,903,884 A | 9/1975 | Huston et al. | |
| 3,906,950 A | 9/1975 | Cocozza | |
| 3,908,654 A | 9/1975 | Lhoest et al. | |
| 3,950,760 A | 4/1976 | Rauch et al. | |
| 3,951,313 A | 4/1976 | Coniglione | |
| 3,958,249 A | 5/1976 | DeMaine et al. | |
| 3,970,250 A | 7/1976 | Drews | |
| 3,983,740 A | 10/1976 | Danel | |
| 3,993,223 A | 11/1976 | Welker, III et al. | |
| 4,005,435 A | 1/1977 | Lundquist et al. | |
| 4,020,834 A | 5/1977 | Bird | |
| 4,030,492 A | 6/1977 | Simburner | |
| 4,052,986 A | 10/1977 | Scaife | |
| 4,059,384 A | 11/1977 | Holland et al. | |
| D246,574 S | 12/1977 | Meierhoefer | |
| 4,076,021 A | 2/1978 | Thompson | |
| 4,083,368 A | 4/1978 | Freezer | |
| 4,094,317 A | 6/1978 | Wasnich | |
| 4,101,041 A | 7/1978 | Mauro, Jr. et al. | |
| 4,106,503 A | 8/1978 | Rsenthal et al. | |
| 4,109,174 A | 8/1978 | Hodgson | |
| 4,113,809 A | 9/1978 | Abair et al. | |
| D249,958 S | 10/1978 | Meierhoefer | |
| 4,119,096 A | 10/1978 | Drews | |
| 4,121,583 A | 10/1978 | Chen | |
| 4,159,803 A | 7/1979 | Cameto et al. | |
| 4,207,990 A | 6/1980 | Weiler et al. | |
| 4,210,155 A | 7/1980 | Grimes | |
| 4,226,236 A | 10/1980 | Genese | |
| 4,240,081 A | 12/1980 | Devitt | |
| 4,240,417 A | 12/1980 | Holever | |
| 4,248,227 A | 2/1981 | Thomas | |
| 4,261,512 A | 4/1981 | Zierenberg | |
| D259,213 S | 5/1981 | Pagels | |
| 4,268,460 A | 5/1981 | Boiarski et al. | |
| 4,291,838 A * | 9/1981 | Williams | 239/138 |
| 4,294,407 A | 10/1981 | Reichl et al. | |
| 4,298,045 A | 11/1981 | Weiler et al. | |
| 4,299,784 A | 11/1981 | Hense | |
| 4,300,546 A | 11/1981 | Kruber | |
| 4,301,093 A | 11/1981 | Eck | |
| 4,319,155 A | 3/1982 | Makai et al. | |
| 4,334,531 A | 6/1982 | Reichl et al. | |
| 4,336,544 A | 6/1982 | Donald et al. | |
| 4,338,576 A | 7/1982 | Takahashi et al. | |
| 4,368,476 A | 1/1983 | Uehara et al. | |
| 4,368,850 A | 1/1983 | Szekely | |
| 4,374,707 A | 2/1983 | Pollack | |
| 4,389,071 A | 6/1983 | Johnson, Jr. et al. | |
| 4,408,719 A | 10/1983 | Last | |
| 4,428,802 A | 1/1984 | Kanai et al. | |
| 4,431,136 A | 2/1984 | Janner et al. | |
| 4,454,877 A | 6/1984 | Miller et al. | |
| 4,465,234 A | 8/1984 | Maehara et al. | |
| 4,470,412 A | 9/1984 | Nowacki et al. | |
| 4,474,251 A | 10/1984 | Johnson, Jr. | |
| 4,474,326 A | 10/1984 | Takahashi | |
| 4,475,113 A | 10/1984 | Lee et al. | |
| 4,479,609 A | 10/1984 | Maeda et al. | |
| 4,512,341 A | 4/1985 | Lester | |
| 4,530,464 A | 7/1985 | Yamamoto et al. | |
| 4,533,082 A | 8/1985 | Maehara et al. | |
| 4,539,575 A | 9/1985 | Nilsson | |
| 4,544,933 A | 10/1985 | Heinzl | |
| 4,546,361 A | 10/1985 | Brescia et al. | |
| 4,550,325 A | 10/1985 | Viola | |
| 4,566,452 A | 1/1986 | Farr | |
| 4,591,883 A | 5/1986 | Isayama | |
| 4,593,291 A | 6/1986 | Howkins | |
| 4,605,167 A | 8/1986 | Maehara | |
| 4,613,326 A | 9/1986 | Szwarc | |
| 4,620,201 A | 10/1986 | Heinzl et al. | |
| 4,628,890 A | 12/1986 | Freeman | |
| 4,632,311 A | 12/1986 | Nakane et al. | |
| 4,658,269 A | 4/1987 | Rezanka | |
| 4,659,014 A | 4/1987 | Soth et al. | |
| 4,677,975 A | 7/1987 | Edgar et al. | |
| 4,678,680 A | 7/1987 | Abowitz | |
| 4,679,551 A | 7/1987 | Anthony | |
| 4,681,264 A | 7/1987 | Johnson, Jr. | |
| 4,693,853 A | 9/1987 | Falb et al. | |
| 4,702,418 A | 10/1987 | Carter et al. | |
| 4,722,906 A | 2/1988 | Guire | |
| 4,753,579 A | 6/1988 | Murphy | |
| 4,790,479 A | 12/1988 | Matsumoto et al. | |
| 4,793,339 A | 12/1988 | Matsumoto et al. | |
| 4,796,807 A | 1/1989 | Bendig et al. | |
| 4,799,622 A | 1/1989 | Ishikawa et al. | |
| 4,805,609 A | 2/1989 | Roberts et al. | |
| 4,819,629 A | 4/1989 | Jonson | |
| 4,819,834 A | 4/1989 | Thiel | |
| 4,823,784 A | 4/1989 | Bordoni et al. | |
| 4,826,080 A | 5/1989 | Ganser | |
| 4,826,759 A | 5/1989 | Guire et al. | |
| 4,828,886 A | 5/1989 | Hieber | |
| 4,843,445 A | 6/1989 | Stemme | |
| 4,849,303 A | 7/1989 | Graham et al. | |
| 4,850,534 A | 7/1989 | Takahashi et al. | |
| 4,865,006 A | 9/1989 | Nogi et al. | |
| 4,871,489 A | 10/1989 | Ketcham | |
| 4,872,553 A | 10/1989 | Suzuki et al. | |
| 4,877,989 A | 10/1989 | Drews et al. | |

| | | | | | | |
|---|---|---|---|---|---|---|
| 4,888,516 A | 12/1989 | Daeges et al. | | 5,342,504 A | 8/1994 | Hirano et al. |
| 4,922,901 A | 5/1990 | Brooks et al. | | 5,347,998 A | 9/1994 | Hodson et al. |
| 4,926,915 A | 5/1990 | Deussen et al. | | 5,348,189 A | 9/1994 | Cater |
| 4,934,358 A | 6/1990 | Nilsson et al. | | 5,350,116 A | 9/1994 | Cater |
| 4,954,225 A | 9/1990 | Bakewell | | 5,355,872 A * | 10/1994 | Riggs et al. ............. 128/200.21 |
| 4,957,239 A | 9/1990 | Tempelman | | 5,357,946 A * | 10/1994 | Kee et al. ............... 128/200.24 |
| 4,964,521 A | 10/1990 | Wieland et al. | | 5,372,126 A | 12/1994 | Blau |
| D312,209 S | 11/1990 | Morrow et al. | | 5,383,906 A | 1/1995 | Burchett et al. |
| 4,968,299 A | 11/1990 | Ahlstrand et al. | | 5,388,571 A * | 2/1995 | Roberts et al. ......... 128/203.12 |
| 4,971,665 A | 11/1990 | Sexton | | 5,388,572 A * | 2/1995 | Mulhauser et al. ..... 128/203.15 |
| 4,973,493 A | 11/1990 | Guire | | 5,392,768 A | 2/1995 | Johansson et al. |
| 4,976,259 A | 12/1990 | Higson et al. | | 5,396,883 A | 3/1995 | Knupp et al. |
| 4,979,959 A | 12/1990 | Guire | | 5,414,075 A | 5/1995 | Swan et al. |
| 4,994,043 A | 2/1991 | Ysebaert | | 5,415,161 A | 5/1995 | Ryder |
| 5,002,048 A | 3/1991 | Makiej, Jr. | | 5,419,315 A | 5/1995 | Rubsamen |
| 5,002,582 A | 3/1991 | Guire et al. | | 5,426,458 A | 6/1995 | Wenzel et al. |
| 5,007,419 A | 4/1991 | Weinstein et al. | | 5,431,155 A | 7/1995 | Marelli |
| 5,016,024 A | 5/1991 | Lam et al. | | 5,435,282 A | 7/1995 | Haber et al. |
| 5,021,701 A | 6/1991 | Takahashi et al. | | 5,435,297 A | 7/1995 | Klein |
| 5,022,587 A | 6/1991 | Hochstein | | 5,437,267 A | 8/1995 | Weinstein et al. |
| 5,024,733 A | 6/1991 | Abys et al. | | 5,445,141 A | 8/1995 | Kee et al. |
| 5,046,627 A | 9/1991 | Hansen | | D362,390 S | 9/1995 | Weiler |
| 5,062,419 A | 11/1991 | Rider | | 5,449,502 A | 9/1995 | Igusa et al. |
| 5,063,396 A | 11/1991 | Shiokawa et al. | | 5,452,711 A | 9/1995 | Gault |
| 5,063,922 A * | 11/1991 | Hakkinen ............... 128/200.16 | | 5,458,135 A | 10/1995 | Patton et al. |
| 5,073,484 A | 12/1991 | Swanson et al. | | 5,458,289 A | 10/1995 | Cater |
| 5,076,266 A | 12/1991 | Babaev | | 5,474,059 A | 12/1995 | Cooper |
| 5,080,093 A | 1/1992 | Raabe et al. | | 5,477,992 A | 12/1995 | Jinks et al. |
| 5,080,649 A | 1/1992 | Vetter | | 5,479,920 A | 1/1996 | Piper et al. |
| 5,086,765 A * | 2/1992 | Levine .................. 128/200.21 | | 5,482,030 A * | 1/1996 | Klein .................... 128/200.23 |
| 5,086,785 A | 2/1992 | Gentile et al. | | 5,485,850 A | 1/1996 | Dietz |
| 5,099,833 A * | 3/1992 | Michaels ................ 128/200.14 | | 5,487,378 A | 1/1996 | Robertson et al. |
| 5,115,803 A | 5/1992 | Sioutas | | 5,489,266 A | 2/1996 | Grimard |
| 5,115,971 A | 5/1992 | Greenspan et al. | | 5,497,944 A | 3/1996 | Weston et al. |
| D327,008 S | 6/1992 | Friedman | | D369,212 S | 4/1996 | Snell |
| 5,122,116 A | 6/1992 | Kriesel et al. | | 5,508,269 A | 4/1996 | Smith et al. |
| 5,129,579 A | 7/1992 | Conte | | 5,511,726 A | 4/1996 | Greenspan et al. |
| 5,134,993 A | 8/1992 | Van Der Linden et al. | | 5,512,329 A | 4/1996 | Guire et al. |
| 5,139,016 A | 8/1992 | Waser | | 5,512,474 A | 4/1996 | Clapper et al. |
| 5,140,740 A | 8/1992 | Weigelt | | 5,515,841 A | 5/1996 | Robertson et al. |
| 5,147,073 A | 9/1992 | Cater | | 5,515,842 A | 5/1996 | Ramseyer et al. |
| 5,152,456 A | 10/1992 | Ross et al. | | 5,516,043 A | 5/1996 | Manna et al. |
| 5,157,372 A | 10/1992 | Langford | | 5,518,179 A | 5/1996 | Humberstone et al. |
| 5,164,740 A | 11/1992 | Ivri | | 5,529,055 A | 6/1996 | Gueret |
| 5,169,029 A | 12/1992 | Behar et al. | | 5,533,497 A | 7/1996 | Ryder |
| 5,170,782 A | 12/1992 | Kocinski | | 5,542,410 A | 8/1996 | Goodman et al. |
| 5,180,482 A | 1/1993 | Abys et al. | | 5,549,102 A | 8/1996 | Lintl et al. |
| 5,186,164 A | 2/1993 | Raghuprasad | | 5,560,837 A | 10/1996 | Trueba |
| 5,186,166 A | 2/1993 | Riggs et al. | | 5,563,056 A | 10/1996 | Swan et al. |
| 5,198,157 A | 3/1993 | Bechet | | D375,352 S | 11/1996 | Bologna |
| 5,201,322 A | 4/1993 | Henry et al. | | 5,570,682 A * | 11/1996 | Johnson ................. 128/200.14 |
| 5,213,860 A | 5/1993 | Laing | | 5,579,757 A | 12/1996 | McMahon et al. |
| 5,217,148 A | 6/1993 | Cater | | 5,582,330 A | 12/1996 | Iba |
| 5,217,492 A | 6/1993 | Guire et al. | | 5,584,285 A * | 12/1996 | Salter et al. ............. 128/200.21 |
| 5,227,168 A | 7/1993 | Chvapil | | 5,586,550 A * | 12/1996 | Ivri et al. ............... 128/200.16 |
| 5,230,496 A | 7/1993 | Shillington et al. | | 5,588,166 A | 12/1996 | Burnett |
| 5,241,954 A * | 9/1993 | Glenn .................. 128/200.18 | | 5,598,836 A * | 2/1997 | Larson et al. .......... 128/200.23 |
| 5,245,995 A | 9/1993 | Sullivan et al. | | 5,601,077 A | 2/1997 | Imbert |
| 5,248,087 A | 9/1993 | Dressler | | 5,609,798 A | 3/1997 | Liu et al. |
| 5,258,041 A | 11/1993 | Guire et al. | | 5,617,844 A * | 4/1997 | King .................... 128/200.18 |
| 5,261,601 A | 11/1993 | Ross et al. | | 5,632,878 A | 5/1997 | Kitano |
| 5,263,992 A | 11/1993 | Guire | | 5,635,096 A | 6/1997 | Singer et al. |
| 5,279,568 A | 1/1994 | Cater | | 5,637,460 A | 6/1997 | Swan et al. |
| 5,297,734 A | 3/1994 | Toda | | 5,647,349 A | 7/1997 | Ohki et al. |
| 5,299,739 A | 4/1994 | Takahashi et al. | | 5,653,227 A | 8/1997 | Barnes et al. |
| 5,303,854 A | 4/1994 | Cater | | 5,654,007 A | 8/1997 | Johnson et al. |
| 5,309,135 A | 5/1994 | Langford | | 5,654,162 A | 8/1997 | Guire et al. |
| 5,312,281 A | 5/1994 | Takahashi et al. | | 5,654,460 A | 8/1997 | Rong |
| 5,313,955 A | 5/1994 | Rodder | | 5,657,926 A | 8/1997 | Toda |
| 5,319,971 A | 6/1994 | Osswald et al. | | 5,660,166 A | 8/1997 | Lloyd |
| 5,320,603 A | 6/1994 | Vetter et al. | | 5,664,557 A | 9/1997 | Makiej, Jr. |
| 5,322,057 A * | 6/1994 | Raabe et al. ........... 128/203.12 | | 5,664,706 A | 9/1997 | Cater |
| 5,342,011 A | 8/1994 | Short | | 5,665,068 A | 9/1997 | Takamura |

| Patent | Date | Name | | Patent | Date | Name |
|---|---|---|---|---|---|---|
| 5,666,946 A | 9/1997 | Langenback | | 6,139,674 A | 10/2000 | Markham et al. |
| 5,670,999 A | 9/1997 | Takeuchi et al. | | 6,142,146 A | 11/2000 | Abrams et al. |
| 5,685,491 A | 11/1997 | Marks et al. | | 6,145,963 A | 11/2000 | Pidwerbecki et al. |
| 5,692,644 A | 12/1997 | Gueret | | 6,146,915 A | 11/2000 | Pidwerbecki et al. |
| 5,694,920 A * | 12/1997 | Abrams et al. ......... 128/200.16 | | 6,152,130 A | 11/2000 | Abrams et al. |
| 5,707,818 A | 1/1998 | Chudzik et al. | | 6,155,676 A | 12/2000 | Etheridge et al. |
| 5,709,202 A | 1/1998 | Lloyd et al. | | 6,158,431 A | 12/2000 | Poole |
| 5,714,360 A | 2/1998 | Swan et al. | | 6,161,536 A | 12/2000 | Redmon et al. |
| 5,714,551 A | 2/1998 | Bezwada et al. | | 6,163,588 A | 12/2000 | Matsumoto et al. |
| 5,718,222 A | 2/1998 | Lloyd et al. | | 6,182,662 B1 | 2/2001 | McGhee |
| D392,184 S | 3/1998 | Weiler | | 6,186,141 B1 | 2/2001 | Pike et al. |
| 5,724,957 A | 3/1998 | Rubsamen et al. | | 6,196,218 B1 | 3/2001 | Voges |
| 5,744,515 A | 4/1998 | Clapper | | 6,196,219 B1 | 3/2001 | Hess et al. |
| 5,752,502 A | 5/1998 | King | | 6,205,999 B1 * | 3/2001 | Ivri et al. ............... 128/200.22 |
| 5,755,218 A | 5/1998 | Johansson et al. | | 6,216,025 B1 * | 4/2001 | Kruger ...................... 600/407 |
| 5,758,637 A * | 6/1998 | Ivri et al. ............... 128/200.16 | | 6,216,916 B1 * | 4/2001 | Maddox et al. ............ 222/105 |
| 5,775,506 A | 7/1998 | Grabenkort | | 6,223,746 B1 | 5/2001 | Jewett et al. |
| 5,788,665 A | 8/1998 | Sekins | | 6,235,177 B1 | 5/2001 | Borland et al. |
| 5,788,819 A | 8/1998 | Onishi et al. | | 6,254,219 B1 | 7/2001 | Agarwal et al. |
| 5,790,151 A | 8/1998 | Mills | | 6,260,549 B1 * | 7/2001 | Sosiak ................... 128/200.23 |
| 5,797,389 A * | 8/1998 | Ryder ................... 128/200.21 | | 6,269,810 B1 * | 8/2001 | Brooker et al. ......... 128/203.12 |
| 5,810,004 A | 9/1998 | Ohki et al. | | 6,270,473 B1 | 8/2001 | Schwebel |
| 5,819,730 A | 10/1998 | Stone et al. | | 6,273,342 B1 | 8/2001 | Terada et al. |
| 5,823,179 A * | 10/1998 | Grychowski et al. ... 128/200.18 | | 6,315,397 B2 | 11/2001 | Truninger et al. |
| 5,823,428 A | 10/1998 | Humberstone et al. | | 6,318,361 B1 * | 11/2001 | Sosiak ................... 128/200.23 |
| 5,829,723 A | 11/1998 | Brunner et al. | | 6,318,640 B1 | 11/2001 | Coffee |
| 5,836,515 A | 11/1998 | Fonzes | | 6,328,030 B1 | 12/2001 | Kidwell et al. |
| 5,839,617 A | 11/1998 | Cater et al. | | 6,328,033 B1 | 12/2001 | Avrahami |
| 5,842,468 A | 12/1998 | Denyer et al. | | 6,336,453 B1 * | 1/2002 | Scarrott et al. ......... 128/200.23 |
| 5,848,587 A * | 12/1998 | King ................... 128/200.18 | | 6,341,732 B1 | 1/2002 | Martin et al. |
| 5,862,802 A * | 1/1999 | Bird ................... 128/204.18 | | 6,358,058 B1 | 3/2002 | Strupat et al. |
| 5,865,171 A * | 2/1999 | Cinquin ................. 128/203.12 | | 6,387,886 B1 | 5/2002 | Montgomery et al. |
| 5,878,900 A | 3/1999 | Hansen | | 6,394,363 B1 | 5/2002 | Arnott et al. |
| 5,893,515 A | 4/1999 | Hahn et al. | | 6,402,046 B1 | 6/2002 | Loser |
| 5,894,841 A | 4/1999 | Voges | | 6,405,934 B1 | 6/2002 | Hess et al. |
| 5,897,008 A | 4/1999 | Hansen | | 6,412,481 B1 * | 7/2002 | Bienvenu et al. ........ 128/200.21 |
| 5,910,698 A | 6/1999 | Yagi | | 6,427,682 B1 | 8/2002 | Klimowicz et al. |
| 5,915,377 A | 6/1999 | Coffee | | 6,443,146 B1 | 9/2002 | Voges |
| 5,918,637 A | 7/1999 | Fleischman | | 6,443,366 B1 | 9/2002 | Hirota et al. |
| 5,921,232 A * | 7/1999 | Yokoi et al. ............ 128/200.14 | | 6,467,476 B1 | 10/2002 | Ivri et al. |
| 5,925,019 A | 7/1999 | Ljungquist | | 6,516,798 B1 * | 2/2003 | Davies ................... 128/201.13 |
| 5,938,117 A * | 8/1999 | Ivri ................... 239/4 | | 6,530,370 B1 | 3/2003 | Heinonen |
| 5,950,619 A | 9/1999 | Van Der Linden et al. | | 6,539,937 B1 * | 4/2003 | Haveri ................... 128/200.21 |
| 5,954,268 A | 9/1999 | Joshi et al. | | 6,540,153 B1 | 4/2003 | Ivri |
| 5,960,792 A | 10/1999 | Lloyd et al. | | 6,540,154 B1 | 4/2003 | Ivri et al. |
| 5,964,417 A | 10/1999 | Amann et al. | | 6,543,443 B1 | 4/2003 | Klimowicz et al. |
| 5,970,974 A | 10/1999 | Van Der Linden et al. | | 6,546,927 B2 | 4/2003 | Litherland et al. |
| 5,976,344 A | 11/1999 | Abys et al. | | 6,550,472 B2 | 4/2003 | Litherland et al. |
| 5,993,805 A | 11/1999 | Sutton et al. | | 6,554,201 B2 | 4/2003 | Klimowicz et al. |
| 6,000,396 A | 12/1999 | Melker et al. | | 6,578,571 B1 * | 6/2003 | Watt ................... 128/200.14 |
| 6,006,745 A * | 12/1999 | Marecki ................. 128/200.23 | | 6,581,595 B1 | 6/2003 | Murdock et al. |
| 6,007,518 A | 12/1999 | Kriesel et al. | | 6,596,261 B1 * | 7/2003 | Adjei et al. ................... 424/45 |
| 6,012,450 A * | 1/2000 | Rubsamen ............. 128/200.14 | | 6,598,602 B1 * | 7/2003 | Sjoholm ................. 128/200.16 |
| 6,014,970 A * | 1/2000 | Ivri et al. ............... 128/200.16 | | 6,601,581 B1 * | 8/2003 | Babaev ................. 128/200.16 |
| 6,026,809 A | 2/2000 | Abrams et al. | | 6,612,303 B1 * | 9/2003 | Grychowski et al. ... 128/200.21 |
| 6,029,666 A | 2/2000 | Aloy et al. | | 6,615,824 B2 | 9/2003 | Power |
| 6,032,665 A | 3/2000 | Psaros | | 6,629,646 B1 | 10/2003 | Ivri |
| 6,037,587 A | 3/2000 | Dowell et al. | | 6,640,804 B2 | 11/2003 | Ivri |
| 6,039,696 A | 3/2000 | Bell | | 6,644,304 B2 * | 11/2003 | Grychowski et al. ... 128/200.18 |
| 6,044,841 A * | 4/2000 | Verdun et al. .......... 128/200.18 | | 6,651,650 B1 | 11/2003 | Yamamoto et al. |
| 6,045,215 A | 4/2000 | Coulman | | 6,694,978 B1 * | 2/2004 | Bennarsten ............ 128/204.21 |
| 6,045,874 A | 4/2000 | Himes | | 6,705,315 B2 | 3/2004 | Sullivan et al. |
| 6,047,818 A | 4/2000 | Warby et al. | | 6,732,944 B2 | 5/2004 | Litherland et al. |
| 6,055,869 A | 5/2000 | Stemme et al. | | 6,745,768 B2 | 6/2004 | Colla et al. |
| 6,060,128 A | 5/2000 | Kim et al. | | 6,745,770 B2 | 6/2004 | McAuliffe et al. |
| 6,062,212 A * | 5/2000 | Davison et al. ........ 128/200.16 | | 6,755,189 B2 | 6/2004 | Ivri et al. |
| 6,068,148 A | 5/2000 | Weiler | | 6,761,161 B2 * | 7/2004 | Scarrott et al. ......... 128/200.14 |
| 6,085,740 A | 7/2000 | Ivri et al. | | 6,769,626 B1 | 8/2004 | Haveri |
| 6,096,011 A | 8/2000 | Trombley, III et al. | | 6,776,155 B2 | 8/2004 | Farrell et al. |
| 6,105,877 A | 8/2000 | Coffee | | 6,782,886 B2 | 8/2004 | Narayan et al. |
| 6,106,504 A | 8/2000 | Urrutia | | 6,810,876 B2 | 11/2004 | Berthon-Jones |
| 6,116,234 A | 9/2000 | Genova et al. | | 6,814,071 B2 | 11/2004 | Klimowicz et al. |
| 6,123,413 A | 9/2000 | Agarwal et al. | | 6,817,361 B2 | 11/2004 | Berthon-Jones et al. |

| | | | |
|---|---|---|---|
| 6,840,240 B1 | 1/2005 | Berthon-Jones et al. | |
| 6,845,770 B2 | 1/2005 | Klimowicz et al. | |
| 6,851,626 B2 | 2/2005 | Patel et al. | |
| 6,860,268 B2 | 3/2005 | Bohn et al. | |
| 6,915,962 B2 | 7/2005 | Power et al. | |
| 6,921,020 B2 | 7/2005 | Ivri | |
| 6,926,208 B2 | 8/2005 | Ivri | |
| 6,948,491 B2 * | 9/2005 | Loeffler et al. | 128/200.14 |
| 6,968,840 B2 | 11/2005 | Smith et al. | |
| 6,978,941 B2 | 12/2005 | Litherland et al. | |
| 7,100,600 B2 | 9/2006 | Loeffler et al. | |
| 2001/0013554 A1 | 8/2001 | Borland et al. | |
| 2001/0015737 A1 | 8/2001 | Truninger et al. | |
| 2002/0011247 A1 | 1/2002 | Ivri et al. | |
| 2002/0023639 A1 | 2/2002 | Ivri et al. | |
| 2002/0023650 A1 | 2/2002 | Gunaratnam et al. | |
| 2002/0033178 A1 | 3/2002 | Farrell et al. | |
| 2002/0036601 A1 | 3/2002 | Puckeridge et al. | |
| 2002/0078958 A1 | 6/2002 | Stenzler | |
| 2002/0088461 A1 * | 7/2002 | Alksnis | 128/203.13 |
| 2002/0104530 A1 | 8/2002 | Ivri et al. | |
| 2002/0121274 A1 | 9/2002 | Borland et al. | |
| 2002/0134372 A1 * | 9/2002 | Loeffler et al. | 128/200.14 |
| 2002/0134374 A1 | 9/2002 | Loeffler et al. | |
| 2002/0134375 A1 | 9/2002 | Loeffler et al. | |
| 2002/0134377 A1 | 9/2002 | Loeffler et al. | |
| 2002/0162551 A1 * | 11/2002 | Litherland | 128/200.14 |
| 2002/0162554 A1 * | 11/2002 | Loescher | 128/205.24 |
| 2002/0195107 A1 | 12/2002 | Smaldone | |
| 2003/0140921 A1 | 7/2003 | Smith et al. | |
| 2003/0145859 A1 | 8/2003 | Bohn et al. | |
| 2003/0150446 A1 | 8/2003 | Patel et al. | |
| 2003/0226906 A1 | 12/2003 | Ivri | |
| 2004/0000598 A1 | 1/2004 | Ivri | |
| 2004/0004133 A1 | 1/2004 | Ivri et al. | |
| 2004/0011358 A1 | 1/2004 | Smaldone et al. | |
| 2004/0035413 A1 | 2/2004 | Smaldone et al. | |
| 2004/0035490 A1 | 2/2004 | Power | |
| 2004/0050947 A1 | 3/2004 | Power et al. | |
| 2004/0123974 A1 | 7/2004 | Marler et al. | |
| 2004/0139963 A1 | 7/2004 | Ivri et al. | |
| 2004/0139968 A1 | 7/2004 | Loeffler et al. | |
| 2004/0188534 A1 | 9/2004 | Litherland et al. | |
| 2004/0194783 A1 | 10/2004 | McAuliffe et al. | |
| 2004/0226561 A1 | 11/2004 | Colla et al. | |
| 2004/0226566 A1 | 11/2004 | Gunaratnam et al. | |
| 2004/0256488 A1 | 12/2004 | Loeffler et al. | |
| 2005/0011514 A1 | 1/2005 | Power et al. | |
| 2005/0039746 A1 | 2/2005 | Grychowski et al. | |
| 2005/0139211 A1 | 6/2005 | Alston et al. | |
| 2005/0150496 A1 | 7/2005 | Smaldone | |
| 2005/0172954 A1 | 8/2005 | Smith et al. | |
| 2005/0178847 A1 | 8/2005 | Power et al. | |
| 2005/0211245 A1 | 9/2005 | Smaldone et al. | |
| 2005/0211253 A1 | 9/2005 | Smaldone et al. | |
| 2005/0217666 A1 | 10/2005 | Fink et al. | |
| 2005/0220763 A1 | 10/2005 | Condos et al. | |
| 2005/0229927 A1 | 10/2005 | Fink et al. | |
| 2005/0229928 A1 | 10/2005 | Ivri et al. | |
| 2005/0235987 A1 | 10/2005 | Smaldone et al. | |
| 2005/0279851 A1 | 12/2005 | Ivri | |

FOREIGN PATENT DOCUMENTS

| | | |
|---|---|---|
| CH | 477 855 | 9/1969 |
| CH | 555 681 | 11/1974 |
| DE | 1 103 522 | 3/1961 |
| DE | 11 03 522 | 3/1961 |
| EP | 0 049 636 A1 | 4/1982 |
| EP | 0 103 161 A2 | 3/1984 |
| EP | 0 134 847 A1 | 3/1985 |
| EP | 0 178 925 A2 | 4/1986 |
| EP | 0 387 222 A1 | 9/1990 |
| EP | 0 432 992 A1 | 6/1991 |
| EP | 0 476 991 B1 | 3/1992 |
| EP | 0 480 615 A1 | 4/1992 |
| EP | 0 510 648 A2 | 10/1992 |
| EP | 0 516 565 A1 | 12/1992 |
| EP | 0 542 723 A2 | 5/1993 |
| EP | 0 933 138 A2 | 4/1999 |
| EP | 0 923 957 A1 | 6/1999 |
| EP | 1 142 600 A1 | 10/2001 |
| FR | 2622113 A | 4/1989 |
| FR | 2624017 A | 6/1989 |
| GB | 973 458 | 10/1964 |
| GB | 1 454 597 | 11/1976 |
| GB | 2 073 616 A | 10/1981 |
| GB | 2 101 500 | 1/1983 |
| GB | 2 177 623 A | 1/1987 |
| GB | 2 240 494 A | 7/1991 |
| GB | 2 272 389 A | 5/1994 |
| JP | 57-023852 | 2/1982 |
| JP | 57-105608 | 7/1982 |
| JP | 58-061857 | 4/1983 |
| JP | 58-139757 | 8/1983 |
| JP | 59-142163 A | 8/1984 |
| JP | 60-004714 | 1/1985 |
| JP | 61-008357 A | 1/1986 |
| JP | 61-215059 A | 9/1986 |
| JP | 02-135169 | 5/1990 |
| JP | 02-189161 | 7/1990 |
| JP | 60-07721 A | 1/1994 |
| WO | WO 82/03548 A | 10/1982 |
| WO | WO 92/07600 A1 | 5/1992 |
| WO | WO 92/11050 A1 | 9/1992 |
| WO | WO 92/17231 A1 | 10/1992 |
| WO | WO 93/01404 A1 | 1/1993 |
| WO | WO 93/10910 A1 | 6/1993 |
| WO | WO 94/09912 A1 | 5/1994 |
| WO | WO 96/09229 | 3/1996 |
| WO | WO97/07896 | 3/1997 |
| WO | WO 99/17888 | 4/1999 |
| WO | WO99/63946 | 12/1999 |
| WO | WO 00/37132 | 6/2000 |
| WO | WO01/18280 | 3/2001 |
| WO | WO 03/059424 A1 | 7/2003 |

OTHER PUBLICATIONS

Siemens, "Servo Ultra Nebulizer 345 Operating Manual," pp. 1-23.

Abys, J.A. et al., "Annealing Behavior of Palladium-Nickel Alloy Electrodeposits," Plating and Surface Finishing, Aug. 1996, pp. 1-7.

Allen, T. *Particle Size Measurement*, Third Edition, Chapman and Hall pp. 167-169 (1981).

Ashgriz, N. et al. "Development of a Controlled Spray Generator" Rev. Sci. Instrum., 1987, pp. 1291-1296, vol. 58, No. 7.

Berggren, E. "Pilot Study of Nebulized Surfactant Therapy for Neonatal Respiratory Distress Syndrome", Acta Paediatr 89: 460-464, Taylor & Francis, ISSN 0803-5253, 2000, Sweden.

Berglund, R.N., et al. "Generation of Monodisperse Aerosol Standards" Environ. Sci. Technology, Feb. 1973, pp. 147-153, vol. 7, No. 2.

Cipolla, D.C. et al., "Assessment of Aerosol Delivery Systems for Recombinant Human Deoxyribonuclease," S.T.P. Pharma Sciences 4 (1) 50-62, 1994.

Cipolla, D.C. et al., "Characterization of Aerosols of Human Recombinant Deoxyribonuclease I (rhDNase) Generated by Neulizers," Pharmaceutical Research II (4) 491-498, 1994.

Dogan, Aydin PhD, Thesis: "Flexional 'Moonie and Cymbal' Actuators", Penn State University, 1994.

Duarte, Alexander G. et al. "Inhalation Therapy During Mechanical Ventilation" Respiratory Care Clinics of North America, Aerosol Therapy, Jun. 2001, pp. 233-259, vol. 7, No. 2.

Fink, James B. et al. "Aerosol Therapy in Mechanically Ventilated Patients: Recent Advances and New Techniques" Seminars in Respiratory and Critical Care Medicine, 2000, pp. 183-201, vol. 21, No. 3.

Fink, James B. et al. Diagram from and abstract or article entitled "Optimizing efficiency of nebulizers during mechanical ventilation: The effect of placement and type of ventilator circuit" Chest, Oct. 1999, 116:312S.

Gaiser Tool Company catalog, pp. 26, 29-30 (1990).

Gonda, I. "Therapeutic Aerosols," Pharmaceutics, The Science of Dosage Form Design, Editor: M.E. Aulton, 341-358, 1988.

Hancock, B.C. et al., "Molecular Mobility of Amorphous Pharmaceutical Solids Below Their Glass Transition Temperatures," Pharmaceutical Research 12, 799-806 (1995).

Heyder, J. et al., "Deposition of particles in the human respiratory tract in the size range 0.005-15 microns." J Aerosol Sci 17: 811-825, 1986.

Hickey, Anthony J. "Pharmaceutical Inhalation Aerosol Technology," Drugs And The Pharmaceutical Science, 1992, pp. 172-173, vol. 54.

Hikayama, H., et al. "Ultrasonic Atomizer with Pump Function" Tech. Rpt. IEICE Japan US88-74:25 (1988).

Jorch, G. Letter to the Editor, "Surfactant Aerosol Treatment of Respiratory Distress Syndrome in Spontaneously Breathing Premature Infants", Pediatric Pulmonology 24: 222-224, 1997, Wiley-Liss.

Maehara, N. et al. "Atomizing rate control of a multi-pinhole-plate ultrasonic atomizer" J. Acoustical Soc. Japan, 1988, pp. 116-121, 44:2.

Maehara, N. et al. "Influence of the vibrating system of a multipinhole-plate ultrasonic nebulizer on its performance" Review of Scientific Instruments, Nov. 1986, p. 2870-2876, vol. 57, No. 1.

Maehara, N. et al. "Influences of liquid's physical properties on the characteristics of a multi-pinhole-plate ultrasonic atomizer" J. Acoustical Soc. Japan 1988, pp. 425-431, 44:6.

Maehara, N. et al. "Optimum Design Procedure for Multi-Pinhole-Plate Ultrasonic Atomizer" Japanese Journal of Applied Physics, 1987, pp. 215-217, vol. 26, Supplement 26-1.

Nogi, T. et al. "Mixture Formation of Fuel Injection System in Gasoline Engine" Nippon Kikai Gakkai Zenkoku Taikai Koenkai Koen Ronbunshu 69:660-662 (1991).

Palla Tech Pd an Pd Alloy Processes—Procedure for the Analysis of Additive IVS in Palla Tech Plating Solutions by HPLC, Technical Bulletin, Electroplating Chemicals & Services, 029-A, Lucent Technologies,, pp. 1-5, 1996.

Smaldone, G. C. "Aerosolized Antibiotics: Current and Future", Respiratory Care, 2000, vol. 45, No. 6, pp. 667-675.

Smedsaas-Löfvenbert, A. "Nebulization of Drugs in a Nasal CPAP System", Scandinavian University Press, 1999, Acta Paediatr 88: 89-92, Sweden.

TSI Incorporated product catalog. Vibrating Orifice Aerosol Generator (1989).

Ueha, S., et al. "Mechanism of Ultrasonic Atomization Using a Multi-Pinhole Plate" J. Acoust. Soc. Jpn., 1985, pp. 21-26, (E)6,1.

Wehl, Wolfgang R. "Ink-Jet Printing: The Present State of the Art" for Siemens AG, 1989.

Abys, J. A. et al., "Annealing Behavior Of Palladium-Nickel Alloy Electrodeposits," Plating and Surface Finishing, 7 pages, Aug. 1996.

Mercier et al., "Aerosol Delivery of Amikacin by Three Nebulizers of Varying Efficiency in Patients on Mechanical Ventilators." Internet Article (online), May 2004; URL: http://www.aerogen.com/publications/2004.htm.

Palmer et al., Aerosolized antibiotics in mechanically ventilated patients: Deliver and response, 1998, Crit Care Med., vol. 26, No. 1, pp. 31-39.

* cited by examiner

APPARATUS AND METHODS FOR DELIVERY OF MEDICAMENT TO A RESPIRATORY SYSTEM

CROSS-REFERENCES TO RELATED APPLICATIONS

This application claims priority the following U.S. Provisional Patent Applications, the entire disclosures of both of which are herein incorporated by reference in their entireties for all purposes: U.S. Prov. Pat. Appl. No. 60/344,484, entitled "APPARATUS AND METHODS FOR DELIVERY OF MEDICAMENTS TO A RESPIRATORY SYSTEM," filed Nov. 1, 2001 by John S. Power et al.; and U.S. Prov. Pat. Appl. No. 60/381,830, entitled "APPARATUS AND METHODS FOR DELIVERY OF MEDICAMENT TO A RESPIRATORY SYSTEM," filed on May 20, 2002 by John Power et al.

BACKGROUND OF THE INVENTION

This invention relates to apparatus and methods for delivery of medicament to the respiratory system of a patient. In particular, the invention relates to apparatus and methods for use with a nebulizer.

It is known to use a nebulizer to create an aerosol of medication for delivery into the respiratory system of a patient. Typically the medication is placed in a cup which is held over a reservoir of buffer water. A piezoelectric element is vibrated ultrasonically under the buffer water transferring energy to the water, thus causing an aerosol to be formed in the medication cup. Baffles are provided between the medication cup and the airway in an attempt to ensure large particles of medication rain out on the baffles and drip back down into the medication cup.

However, these nebulizers suffer from a number of disadvantages. In particular, medications have a range of different viscosities, but particle generation is not consistent across the range. Thus the medication particle size is not accurately controlled and a broad range of particles pass into the patient airway. Impaction filters/baffles are often used to attempt to "rain-out" larger particles due to impact of the larger particles with the filters/baffles. Nebulized medication which rains out drips back into the cup only to be nebulized again. This impaction of the nebulized medication may degrade or destroy the medication, and this is particularly the case for long molecular structures, such as proteins.

The medication in the cup is directly exposed to the airway. Therefore the nebulizer must be maintained substantially horizontal at all times to prevent medication spilling out into the patient airway. Also the ventilator pressure may be lost when the medication cup is removed to refill it.

This method of aerosol generation requires a relatively large amount of energy. The response time of aerosol generation is therefore large. A considerable amount of heat is generated during use of the nebulizer, therefore to prevent patient discomfort or injury the nebulizer must be placed away from the patient. This necessitates a long inhalation tube between the nebulizer and the patient, which increases drug loss through rain out along the inhalation tube, and further increases the response time to patient inspiration. Furthermore the generated heat degenerates the medication, which can be particularly harmful to protein based drugs.

This invention is related to apparatus and methods for delivery of medicament to the respiratory system of a patient which overcome at least some of these disadvantages.

BRIEF SUMMARY OF THE INVENTION

According to the invention, there is provided an apparatus for delivery of a medicament to a respiratory system, the apparatus comprising a reservoir for a liquid medicament for delivery to a respiratory system, the reservoir having a liquid medicament inlet port and a medicament outlet; an aerosol generator at the medicament outlet of the reservoir for aerosolizing a liquid medicament; and a connector for entraining an aerosolized medicament from the aerosol generator with a gas.

In one embodiment of the invention the inlet port is an upper inlet port and the outlet is a lower outlet for gravitational flow of a liquid medicament from the reservoir to the aerosol generator. In one case the apparatus comprises a plug for selectively sealing the inlet port. The plug may be attached to the reservoir for movement between a sealed position and an open position. Ideally the plug is attached to the reservoir by an arm. The arm may be biased towards the open position.

In one embodiment the arm defines a hinge for pivoting of the plug between the sealed position and the open position. The hinge may be a live hinge.

In another embodiment the plug is integral with the arm. Ideally the arm is integral with at least part of the reservoir.

In another embodiment of the invention the reservoir defines an access opening in a wall of the reservoir to facilitate access to an interior of the reservoir, and the reservoir comprises a cap for mounting at the access opening. The inlet port may be small relative to the access opening. In one case the inlet port is provided through the cap. Ideally the plug is integral with the cap. In one case the cap is mountable at the access opening in a snap-fit arrangement.

In one embodiment the plug seals the inlet port in a snap-fit arrangement.

An interior surface of the reservoir may be configured to promote flow of a liquid medicament towards the aerosol generator. Ideally the interior surface of the reservoir is inclined towards the aerosol generator. The reservoir may define a substantially conical shape at least in the region adjacent the aerosol generator.

In another embodiment of the invention the connector comprises a gas conduit having an inlet and an outlet, and an aerosol supply conduit for delivering an aerosolized medicament from the aerosol generator into the gas conduit to entrain the aerosolized medicament with a gas. The aerosol supply conduit may subtend an angle of less than 90° with the inlet of the gas conduit. In one case the aerosol supply conduit subtends an angle of less than 80° with the inlet of the gas conduit. Ideally the aerosol supply conduit subtends an angle of about 75° with the inlet of the gas conduit.

In another embodiment the aerosol supply conduit is co-axial with the inlet of the gas conduit.

The inlet of the gas conduit may extend co-axially around the aerosol supply conduit.

In another embodiment of the invention, the aerosol supply conduit subtends an angle of 90° with the inlet of the gas conduit.

In one embodiment of the invention the apparatus comprises a respiratory conduit for connecting the outlet of the gas conduit to a respiratory system. The respiratory conduit may be mounted to the connector at the outlet of the gas conduit. In one case the respiratory conduit is releasably mounted to the connector at the outlet of the gas conduit. The respiratory conduit may be mounted to the connector by an interference fit between the respiratory conduit and the outlet of the gas conduit.

In another embodiment of the invention the apparatus comprises an intermediate connector mounted between the respiratory conduit and the outlet of the gas conduit. The intermediate connector may have a lumen extending therethrough, and the cross-sectional area of the lumen may vary along the length of the lumen. Preferably the cross-sectional area of the lumen varies in a discontinuous manner along the length of the lumen.

In one case the respiratory conduit is mounted to the intermediate connector by an interference fit between the respiratory conduit and the intermediate connector. In another case the intermediate connector is mounted to the outlet of the gas conduit by an interference fit between the intermediate connector and the outlet of the gas conduit.

Ideally the intermediate connector comprises handle means for gripping the intermediate connector. The handle means may comprise one or more formations on the intermediate connector. Preferably the formation comprises a protruding flange. Most preferably the handle means comprises two substantially diametrically opposed protruding flanges.

In one embodiment the respiratory conduit is moveable relative to the gas conduit. Ideally the respiratory conduit is rotatable about the longitudinal axis of the outlet of the gas conduit.

In one case the respiratory conduit is selected from a group consisting of a mouthpiece, a face mask, and an inter-tracheal tube. The respiratory conduit may comprise an intermediate portion between the outlet of the gas conduit and the mouthpiece, or the face mask, or the inter-tracheal tube, the intermediate portion being moveable relative to the mouthpiece, or the face mask, or the inter-tracheal tube. In one embodiment the respiratory conduit defines a delivery path to a respiratory system, the delivery path being defined by a distance between the aerosol generator and the respiratory system, the delivery path having a length of less than about 500 mm. The respiratory conduit may have a delivery path of less than about 300 mm.

In one case the delivery path is substantially free of baffles and/or flow disrupters.

In another embodiment the respiratory conduit includes a Y-shaped section which separates into a first arm for inhalation to a respiratory system and a second arm for exhalation from a respiratory system.

The apparatus may comprise a ventilator conduit for connecting the inlet of the gas conduit to a ventilator. In one case the ventilator conduit is mounted to the connector at the inlet of the gas conduit. Ideally the ventilator conduit is releasably mounted to the connector at the inlet of the gas conduit. The ventilator conduit may be mounted to the connector by an interference fit between the ventilator conduit and the inlet of the gas conduit.

In another embodiment of the invention the apparatus comprises an intermediate connector mounted between the ventilator conduit and the inlet of the gas conduit. The intermediate connector may have a lumen extending therethrough, and the cross-sectional area of the lumen may vary along the length of the lumen. Preferably the cross-sectional area of the lumen varies in a discontinuous manner along the length of the lumen.

In one case the ventilator conduit is mounted to the intermediate connector by an interference fit between the ventilator conduit and the intermediate connector. In another case the intermediate connector is mounted to the inlet of the gas conduit by an interference fit between the intermediate connector and the inlet of the gas conduit.

Ideally the intermediate connector comprises handle means for gripping the intermediate connector. The handle means may comprise one or more formations on the intermediate connector. Preferably the formation comprises a protruding flange. Most preferably the handle means comprises two substantially diametrically opposed protruding flanges.

In one embodiment of the invention the apparatus comprises an aerosol generator housing in which the aerosol generator is held, and the connector is mounted to the aerosol generator housing. The connector may be releasably mounted to the aerosol generator housing. Ideally the connector is mounted to the aerosol generator housing by an interference fit between the aerosol generator housing and the aerosol supply conduit. The connector may be mounted to the aerosol generator housing by an interference fit between the aerosol generator housing and the inlet of the gas conduit.

In one case the aerosol generator housing is fixed to the reservoir.

The aerosol generator housing may be integral with the reservoir.

In another case the apparatus comprises a signal interface to receive a control signal to control operation of the aerosol generator. The apparatus may comprise a controller to control operation of the aerosol generator, the controller being connectable to the signal interface. In one embodiment the controller has an on-board power source. The controller may comprise a power connector, the power connector being connectable to a remote power source.

In another embodiment the controller comprises a timer to automatically switch the aerosol generator between an active state and a rest state. The timer may be selectively programmable.

The controller ideally comprises a user interface to selectively control operation of the aerosol generator. The user interface may be remote from the aerosol generator housing.

In another embodiment the controller comprises status indication means to indicate the operational state of the aerosol generator. The status indication means comprises at least one visual indicator.

Ideally the controller comprises a housing having a support to receive a mounting device. The support may comprise a recess in the housing for receiving a mounting device. In one case the support comprises at least one ledge overhanging the recess for engagement of a mounting device in the recess. The support may comprise two ledges on opposite sides of the recess.

In another case the apparatus comprises a mounting device to support the controller. The mounting device may comprise means for attaching the mounting device to a support; and hook means for supporting the housing, the hook means being configured to define a plurality of support surfaces for supporting the housing in an upright configuration. In one embodiment the support surfaces each comprise a lip protruding from a main body of the mounting device. The lip may be engagable in the recess in the housing to support the controller. Ideally the hook means defines four support surfaces. Each support surface may be substantially perpendicular to an adjacent support surface.

In one case the attachment means is releasable. Ideally the attachment means comprises a clamp.

In another embodiment the hook means is movable relative to the attachment means to selectively disassociate the hook means from the attachment means. The attachment means may define a groove in which the hook means is slidable to selectively disassociate the hook means from the attachment means.

In another case the aerosol generator comprises a vibratable member having a plurality of apertures extending between a first surface and a second surface thereof. The first surface may be adapted to receive a liquid medicament from the reservoir. Ideally the aerosol generator is configured to generate an aerosol at the second surface. In one case the vibratable member is dome shaped in geometry. The vibratable member may comprise a piezoelectric element.

In another embodiment the apertures in the vibratable member are sized to aerosolize the medicament by ejecting droplets of medicament such that about 70% or more of the droplets by weight have a size in the range from about 1 to about 5 micrometers.

In another aspect of the invention, there is provided a kit for delivery of a medicament to a respiratory system, the kit comprising an apparatus of the invention; and a supply container for delivering a liquid medicament through the inlet port into the reservoir.

In one embodiment of the invention the supply container defines a delivery tip configured to mate with the inlet port of the reservoir for delivering a liquid medicament through the inlet port into the reservoir. The delivery tip may be configured for insertion at least partially through the inlet port.

In another embodiment the supply container has indication means to indicate the volume of liquid medicament delivered into the reservoir. The indication means may be provided by at least one marking on the supply container.

In one case the supply container comprises a nebule. In another case the supply container comprises a syringe.

According to another aspect, the invention provides a connector for entraining an aerosolized medicament with a gas to deliver the medicament to a respiratory system, the connector comprising a gas conduit having an inlet and an outlet; and an aerosol supply conduit for delivering an aerosolized medicament into the gas conduit to entrain the aerosolized medicament with a gas, the connector comprising a cap to selectively seal the aerosol supply conduit to maintain the pressure in the gas conduit when the connector is not in use.

In one case the cap is attached to the gas conduit.

In a further aspect of the invention, there is provided a method of delivering a medicament to a respiratory system, the method comprising the steps of providing a reservoir for a liquid medicament to be delivered to a respiratory system; delivering a volume of the liquid medicament into the reservoir; providing an aerosol generator for aerosolizing the liquid medicament; arranging the aerosol generator beneath the reservoir for gravitational flow of the liquid medicament from the reservoir to the aerosol generator; aerosolizing the liquid medicament; delivering the aerosolized medicament to the respiratory system.

In one embodiment of the invention the method comprises the step of entraining the aerosolized medicament with a gas before delivering the aerosolized medicament to the respiratory system.

The aerosol generator may be mounted to the reservoir beneath the reservoir.

In another case the method comprises the step of vibrating at least part of the aerosol generator to aerosolize the liquid medicament.

Ideally the method comprises the step of delivering a further volume of the liquid medicament into the reservoir. The further volume of the liquid medicament may be delivered into the reservoir after all of the liquid medicament in the reservoir has been aerosolized. Alternatively the further volume of the liquid medicament may be delivered into the reservoir before all of the liquid medicament in the reservoir has been aerosolized.

In another embodiment the method comprises the step of opening a port to deliver the volume of the liquid medicament through the port into the reservoir. The method may comprise the step of sealing the port after delivering the volume of the liquid medicament into the reservoir. Ideally the port is sealed before the step of aerosolizing the liquid medicament.

The inlet port to the reservoir is distanced from the aerosol generator to create a sterile barrier between the carrier delivering the liquid medicament into the reservoir and the respiratory system of the patient.

The liquid medicament flows by gravitational action from the reservoir to the aerosol generator. This arrangement provides a simple, consistent means of delivering liquid medicament to the aerosol generator, regardless of the viscosity of the liquid medicament.

The reservoir is configured to promote flow of the liquid medicament towards the aerosol generator. This arrangement minimizes the residual volume of the liquid medicament remaining in the reservoir after use, and also enables the volume of the liquid medicament delivered to the respiratory system of the patient to be accurately controlled.

The reservoir may be quickly and easily filled or refilled without requiring dismounting of any parts of the assembled apparatus.

The apparatus of the invention may be quickly and easily cleaned, for example by autoclaving. In particular, the cap may be removed from the relatively large access opening to facilitate cleaning of the interior of the reservoir through the access opening, and also to facilitate egress of material and/or cleaning fluids out of the reservoir through the access opening.

BRIEF DESCRIPTION OF THE DRAWINGS

The invention will be more clearly understood from the following description of some embodiments thereof, given by way of example only, with reference to the accompanying drawings, in which

FIG. 2A provides an expanded schematic sectional view of a vibratable member of the apparatus of FIG. 1;

DETAILED DESCRIPTION OF THE INVENTION

Figure 1:
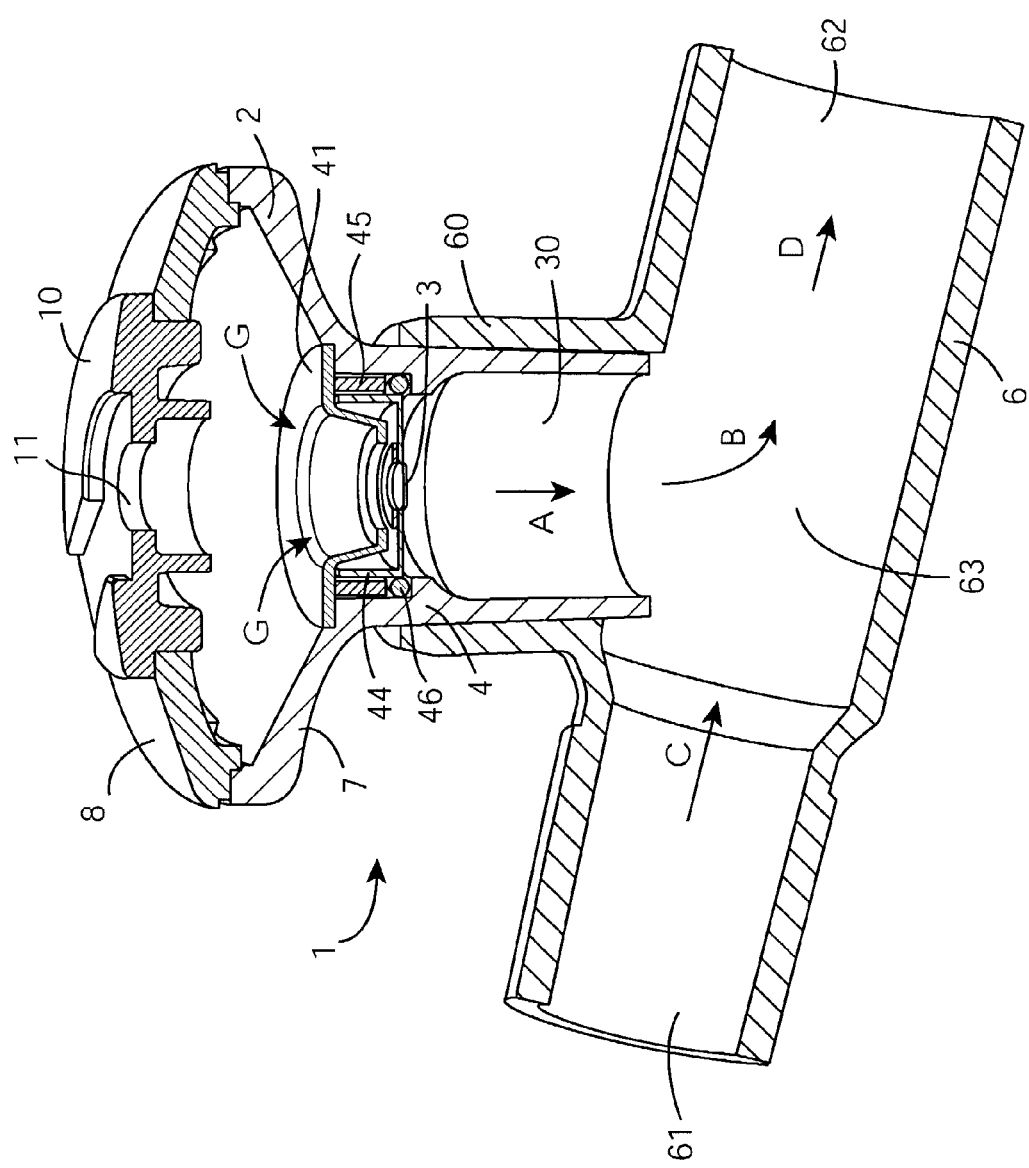
FIG. 1 is a side, cross-sectional view of an apparatus for delivery of a medicament to a respiratory system according to the invention.

Referring to the drawings and initially to FIGS. 1 to 7 thereof, there is illustrated an apparatus 1 according to the invention for delivering a medicament to a respiratory system.

The apparatus 1 comprises a reservoir 2 for a liquid medicament for delivery to a respiratory system, an aerosol generator 3 for aerosolizing the liquid medicament, and a connector 6 for entraining the aerosolized medicament from the aerosol generator 3 with a gas.

Figure 2:
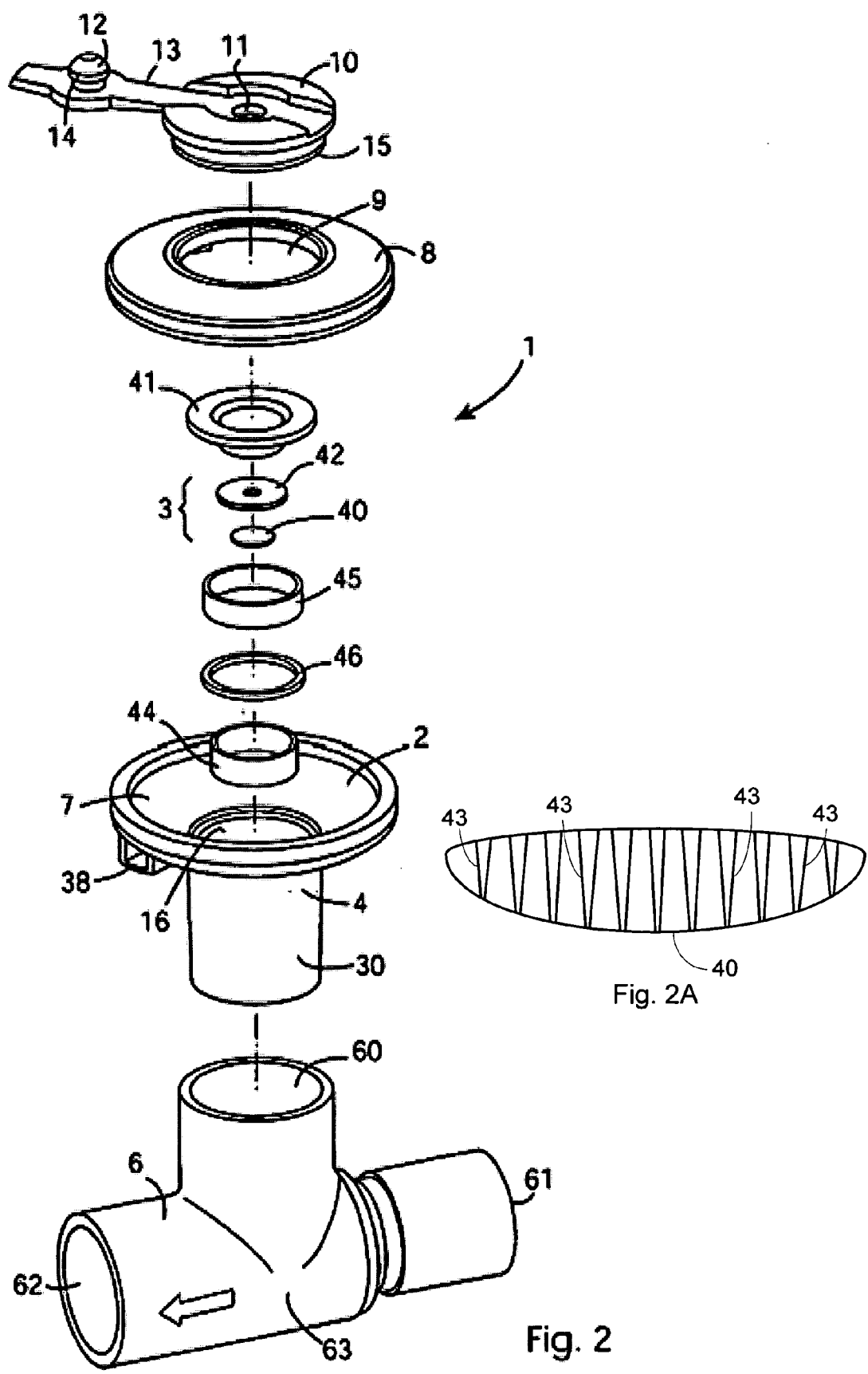
FIG. 2 is an exploded, perspective view of the apparatus of FIG. 1.
Figure 3:
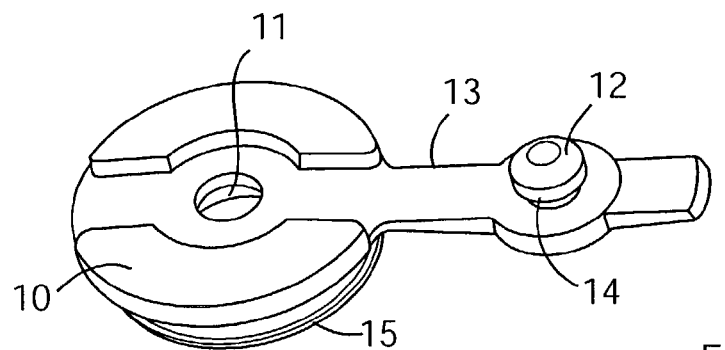
FIG. 3 is a perspective view of a cap of the apparatus of FIGS. 1 and 2.
Figure 4:
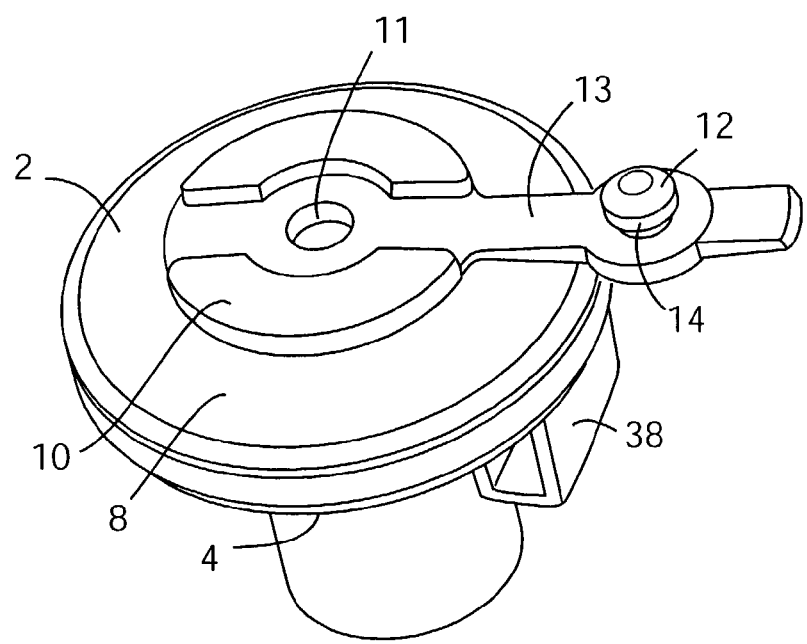
FIG. 4 is a perspective view of the cap of FIG. 3 mounted to a reservoir of the apparatus of FIGS. 1 and 2.

The reservoir 2 comprises a lower portion 7 and an upper portion 8, as illustrated in FIGS. 1 and 2, the two portions 7, 8 being fixed together. The two portions 7, 8 are injection moulded separately, and are then ultrasonically welded together to form the reservoir 2. Alternatively the portions 7, 8 could be integrally manufactured, such as by a CNC machining process.

An access opening 9 is defined in a wall of the upper portion 8 of the reservoir 2 (FIG. 2), the opening 9 facilitating access to the interior of the reservoir 2, for example for cleaning the interior of the reservoir 2. The reservoir 2 comprises a cap 10 for mounting at the access opening 9 to close the opening 9 when the apparatus 1 is in use (FIG. 1). The cap 10 may define a suitable projecting annular lip 15 for snap-fit mounting of the cap 10 at the opening 9.

The reservoir 2 has an upper liquid medicament inlet port 11 for delivering the liquid medicament into the reservoir 2. The inlet port 11, which is small relative to the access opening 9, is provided through the cap 10, as illustrated in FIG. 1.

Figure 5:
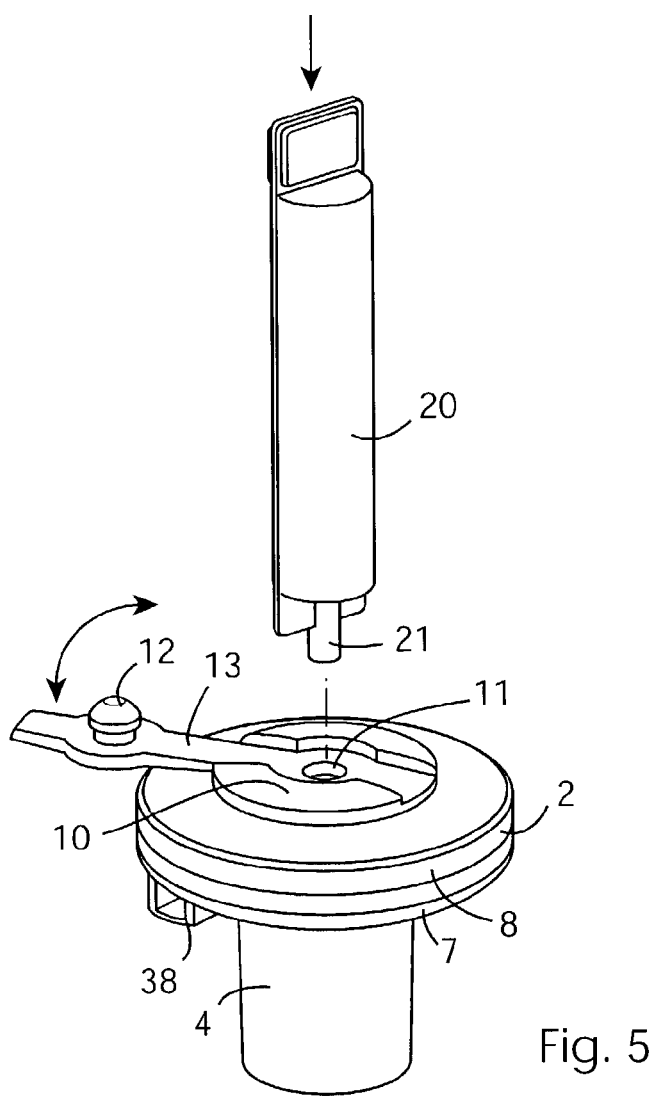
FIGS. 5 and 6 are perspective views illustrating filling of the reservoir of FIG. 4 through the cap.

A plug 12 is provided to seal the inlet port 11, the plug 12 being attached to the cap 10 by an arm 13 for movement of the plug 12 between a sealed position (FIG. 6) and an open position (FIG. 5). The arm 13 includes a hinge for pivoting of the plug 12 between the sealed position and the open position, preferably the hinge is a live hinge to bias the arm 13 towards the open position. A suitable projecting annular shoulder 14 may be provided on the plug 12 for snap-fit sealing of the inlet port 11 by the plug 12.

The cap 10, arm 13 and plug 12 may be integrally formed of a polymeric material in a molding process. One suitable material is a silicone material with a Shore A hardness of between 60 and 80.

The reservoir 2 has a lower medicament outlet 16, and the aerosol generator 3 is positioned, when the apparatus 1 is assembled, at the outlet 16 (FIG. 1). In use, the liquid medicament flows by gravitational action from the reservoir 2 to the aerosol generator 3.

The lower portion 7 of the reservoir 2 is substantially conical shaped, sloping towards the aerosol generator 3 to promote flow of the liquid medicament towards the aerosol generator 3 at the outlet 16 (Flow G), as illustrated in FIG. 1. In this manner, the residual volume of the liquid medicament that remains in the reservoir 2 after use is minimised, and thus the volume of the liquid medicament which is delivered to the respiratory system of the patient is accurately controlled.

A typical volume of liquid medicament that can be held in the reservoir is 10 mL, or 6 mL.

The aerosol generator 3 comprises a vibratable member 40 and a piezoelectric element 42. As shown in the schematic expanded view of FIG. 2A, vibratable member 40 has a plurality of tapered apertures 43 extending between a first surface and a second surface thereof, as described in U.S. Pat. Nos. 5,164,740 5,586,550, 5,758,637, 6,085,740, the entire contents of which are incorporated herein by reference.

The first surface of the vibratable member 40, which in use faces upwardly, receives the liquid medicament from the reservoir 2, and the aerosolised medicament is generated at the second surface of the vibratable member 40 by ejecting droplets of medicament upon vibration of the member 40. In use the second surface faces downwardly. In one case, the apertures in the vibratable member 40 may be sized to produce an aerosol in which about 70% or more of the droplets by weight have a size in the range from about 1 to 5 micrometers.

The vibratable member 40 is non-planar, and is preferably dome-shaped in geometry.

The apparatus 1 comprises an aerosol generator housing 4 fixed to the lower portion 7 of the reservoir 2, for example by integrally manufacturing the housing 4 and the lower portion 7.

In the assembled apparatus of FIG. 1, the aerosol generator 3 is held within the aerosol generator housing 4 between an upper shield 41 and a lower retainer 44. The shield 41, the piezoelectric element 42, and the retainer 44 have central apertures aligned to facilitate flow of the liquid medicament from the reservoir 2 to the aerosol generator 3, and to facilitate passage of the aerosolized medicament from the aerosol generator 3 into a neck 30 of the aerosol generator housing 4.

An O-ring seal 46 and a sleeve 45 are provided between the retainer 44 and the wall of the aerosol generator housing 4 and the shield 41 is fixed to the lower portion 7 of the reservoir 2. An anti-bacterial coating may be applied to the vibratable member 40 to ensure a sterile flow of aerosolized medicament into the neck 30.

The connector 6 comprises a gas conduit having an inlet 61 and an outlet 62, and an aerosol supply conduit 60 for delivering the aerosolised medicament from the aerosol generator 3 into the gas conduit to entrain the aerosolised medicament with a gas, such as air, passing through the gas conduit. The entrained aerosolised medicament/gas mixture passes out of the gas conduit through the outlet 62.

The connector 6 is of a general T-shape, the aerosol supply conduit 60 subtending an angle of about 75° with the inlet 61 of the gas conduit (FIG. 1). The longitudinal axis of the inlet 61 of the gas conduit is co-axial with the longitudinal axis of the outlet 62 of the gas conduit, and the gas conduit tapers slightly outwardly between the inlet 61 and the outlet 62.

It will be appreciated that the angle subtended between the aerosol supply conduit 60 and the inlet 61 of the gas conduit may be any suitable angle in the range of from 60° to 90°, but preferably less than 90°, and most preferably from 60° to 80°, to induce the entrained aerosolized medicament/gas mixture to pass out of the gas conduit through the outlet 62, in particular when the apparatus 1 is used in a floor use non-ventilator application.

The aerosol supply conduit 60 and the gas conduit meet at a junction 63 (FIG. 1). In the assembled apparatus 1, the aerosol supply conduit 60 of the connector 6 is releasably mounted to the neck 30 of the aerosol generator housing 4 by means of a push-fit arrangement. This enables the connector 6 to be easily dismounted from the aerosol generator housing 4, for example for cleaning. The neck 30 at least partially lines the interior of the aerosol supply conduit 60, as illustrated in FIG. 1.

The inlet 61 of the gas conduit may be connected to a ventilator 70 which pumps a gas, such as air, into the gas conduit, alternatively the apparatus 1 may be employed during manual breathing with the inlet 61 of the gas conduit being open to atmosphere.

Figure 7:
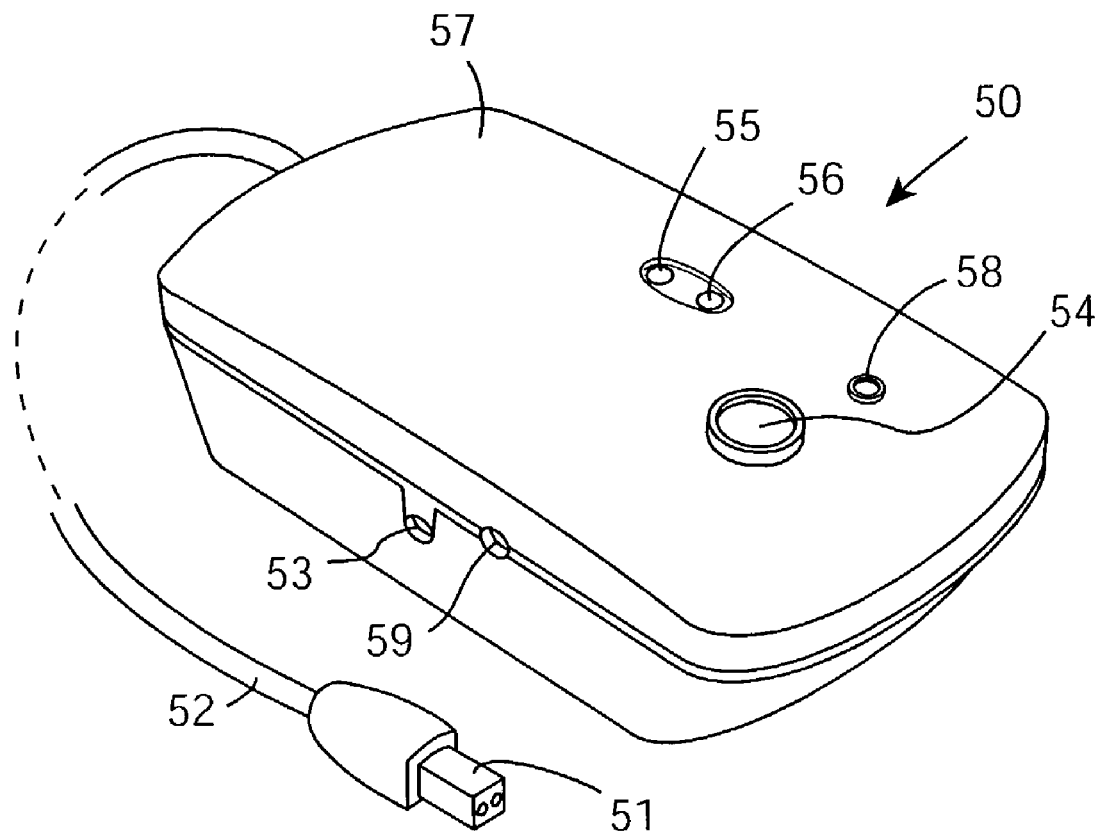
FIG. 7 is a perspective view of a controller of the apparatus of FIGS. 1 and 2.

The apparatus 1 also includes a controller 50 as illustrated in FIG. 7, to control operation of and to supply power to the aerosol generator 3. The reservoir 2 has a signal interface port 38 fixed to the lower portion 7 of the reservoir 2 to receive a control signal from the controller 50. The controller 50 may be connected to the signal interface port 38 by means of a control lead 52 which has a docking member 51 for mating with the port 38. A control signal and power may be passed from the controller 50 through the lead 52 and the port 38 to the aerosol generator 3 to control the operation of the aerosol generator 3 and to supply power to the aerosol generator 3 respectively.

The power source for the controller 50 may be an on-board power source, such as a rechargeable battery, or a remote power source, such as a mains power source, or a ventilator power source. When the remote power source is an AC mains power source, an AC-DC converter may be connected between the AC power source and the controller 50. A power connection lead may be provided to connect a power socket 53 of the controller 50 with the remote power source.

The controller 50 has a housing 57, and a user interface to selectively control operation of the aerosol generator 3. Preferably the user interface is provided on the housing 57 which, in use, is located remote from the aerosol generator housing 4. The user interface may be in the form of, for example, an on-off button 54, or a reset button.

A selectively programmable timer may be provided by the controller 50 to automatically switch the aerosol generator 3 between an active state and a rest state. For example, the timer may be configured to switch the aerosol generator 3 from an active state to a rest state after 15 minutes of aerosol generation. The timer may alternatively be configured to activate generation of the aerosol a short period after commencement of an inhalation cycle, for example within 20 milliseconds, and to cease generation of the aerosol a short period after commencement of an exhalation cycle, for example within 20 milliseconds.

Status indication means are also provided on the housing 57 to indicate the operational state of the aerosol generator 3. For example, the status indication means may be in the form of two visible LED's, with one LED 55 being used to indicate a 15 minute timer cycle, and the other LED 56 being used to indicate a 30 minute timer cycle. Alternatively one LED 55 may be used to indicate an operational state of the aerosol generator 3, and the other LED 56 may be used to indicate a rest state of the aerosol generator 3.

A fault indicator 58 is also provided in the form of an LED on the housing 57. A battery charge indicator 59 in the form of an LED is provided at the side of the housing 57.

In use, the cap 10 is mounted at the access opening 9 in a snap-fit manner to close the opening 9. The plug 12 is then moved from the sealed position (FIG. 6) to the open position (FIG. 5) by hinging the arm 13 to the open position, and a volume of liquid medicament is delivered through the inlet port 11 into the reservoir 2.

Typically a supply container, such as a nebule 20 (FIG. 5) or a syringe, is used to deliver the liquid medicament through the inlet port 11 into the reservoir 2. In the case of nebule 20, a delivery tip 21 is defined at an end of nebule 20 for mating with the inlet port 11 by inserting the delivery tip 21 at least partially through the inlet port 11. In this way, the volume of liquid medicament may be easily and quickly delivered into the reservoir 2. In particular, it is not necessary to dismount any parts of the assembled apparatus 1 to deliver the liquid medicament into the reservoir 2.

Figure 6:
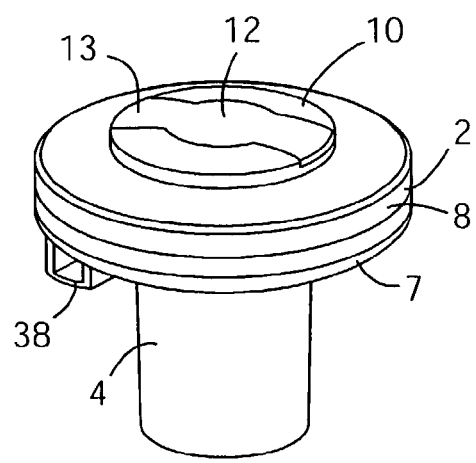

When the desired volume of liquid medicament has been delivered into the reservoir 2, the arm 13 is hinged to the closed position and the inlet port 11 is sealed by the plug 12 (FIG. 6).

The nebule 20 preferably includes markings to indicate the volume of liquid medicament delivered into the reservoir 2. This provides an accurate means of measuring the volume of liquid medicament being delivered to the respiratory system of a patient.

By distancing the inlet port 11 to the reservoir 2 from the aerosol generator 3 at the outlet 16, this arrangement creates a sterile barrier between the carrier delivering the liquid medicament into the reservoir 2 and the respiratory system of the patient.

The liquid medicament in the reservoir 2 flows by gravitational action towards the aerosol generator 3 at the lower medicament outlet 16 (Flow G).

The connector 6 is then releasably mounted to the aerosol generator housing 4 at the aerosol supply conduit 60 by means of an interference fit between the neck 30 of the aerosol generator housing 4 and the aerosol supply conduit 60 of the connector 6 (FIG. 1).

The docking member 51 of the control lead 52 is mated with the signal interface port 38 on the reservoir 2 to connect the controller 50 to the aerosol generator 3. The controller 50 may then be activated to supply power and a control signal to the aerosol generator 3, which causes the piezoelectric element 42 to vibrate the non-planar member 40. This vibration of the non-planar member 40 causes the liquid medicament at the top surface of the member 40 to pass through the apertures to the lower surface where the medicament is aerosolized by the ejection of small droplets of medicament.

The aerosolized medicament passes from the aerosol generator 3 into the neck 30 of the aerosol generator housing 4 (Flow A), which is mounted within the aerosol supply conduit 60 of the connector 6, and into the gas conduit of the connector 6 (Flow B). The aerosolized medicament is entrained in the gas conduit with a gas, such as air, which passes into the gas conduit through the inlet 61 (Flow C). The entrained mixture of the aerosolized medicament and the gas then passes out of the gas conduit through the outlet 62 (Flow D) and on to the respiratory system of the patient.

As the aerosolized medicament is continuously delivered to the respiratory system of the patient, the volume of liquid medicament in the reservoir 2 gradually decreases. The reservoir 2 may be quickly and easily refilled by opening the seal at the inlet port 11 and delivering liquid medicament through the inlet port 11 into the reservoir 2, as described previously with reference to FIGS. 5 and 6. It is not necessary to dismount any parts of the apparatus 1 during refilling of the reservoir 2.

The generation of aerosolized medicament at the aerosol generator 3 may continue during refilling, or alternatively the generation may be temporarily stopped during refilling.

The refill arrangement of the reservoir 2 enables the apparatus 1 to be reused many times.

A suitable material for the connector 6, and for the integral reservoir 2 and aerosol generator housing 4 is polysulphone. By manufacturing these components of the apparatus from polysulphone, this enables these components to be autoclaved for multiple use of the same apparatus. Preferably the connector 6, the reservoir 2 and the aerosol generator housing 4 are suitable to be autoclaved up to 100 times.

An alternative material for the connector 6, and for the integral reservoir 2 and aerosol generator housing 4 is polycarbonate. This reduces the component cost, however the number of times these components can be autoclaved and re-used is also reduced by using polycarbonate.

Figure 8:
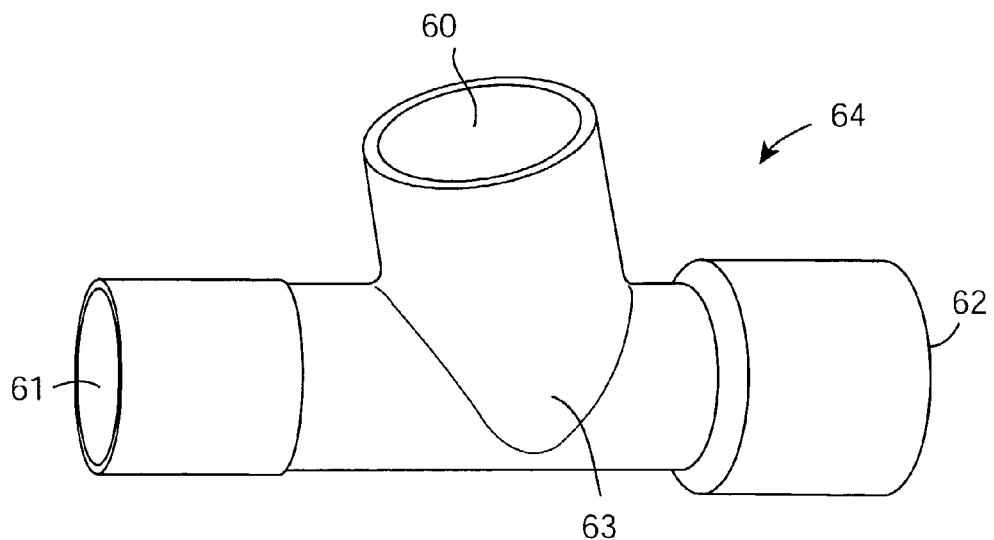
FIG. 8 is a perspective view of an alternative connector of the apparatus of FIGS. 1 and 2.
Figure 9:
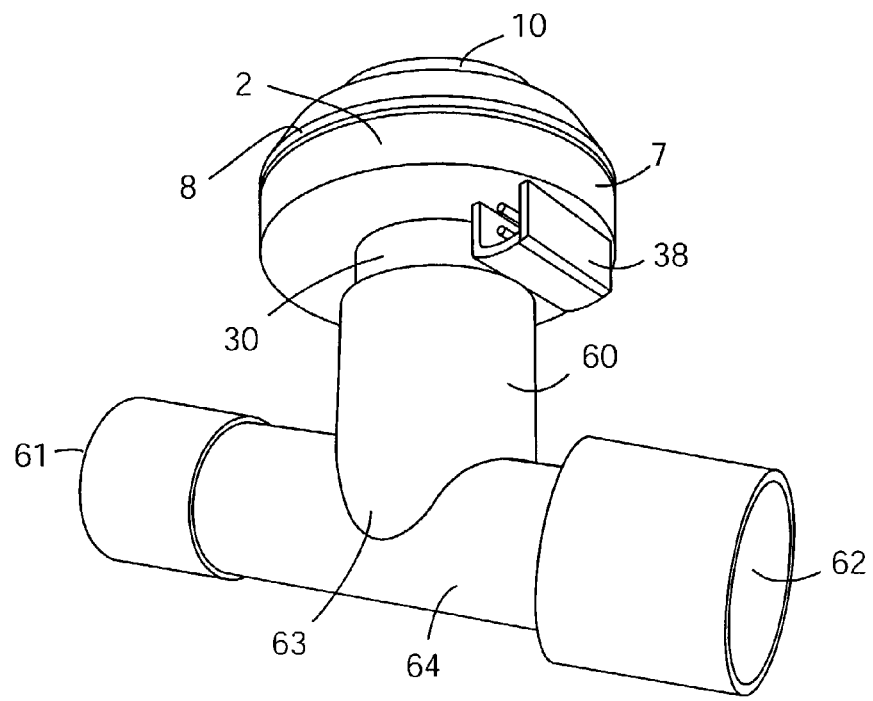
FIG. 9 is a perspective view from beneath of the connector of FIG. 8 mounted to an aerosol generator housing of the apparatus of FIGS. 1 and 2.

Referring now to FIGS. 8 and 9, there is illustrated another connector 64, which is similar to the connector 6 of FIGS. 1 and 2, and similar elements in FIGS. 8 and 9 are assigned the same reference numerals.

The connector 64 may be substituted for the connector 6, and thereafter operation of the apparatus 1 of the invention using the connector 64 proceeds in a manner similar to that described previously with reference to FIGS. 1 to 7. The gas conduit of the connector 64 has a smaller diameter and is longer than the gas conduit of the connector 6 of FIGS. 1 and 2.

Figure 11:
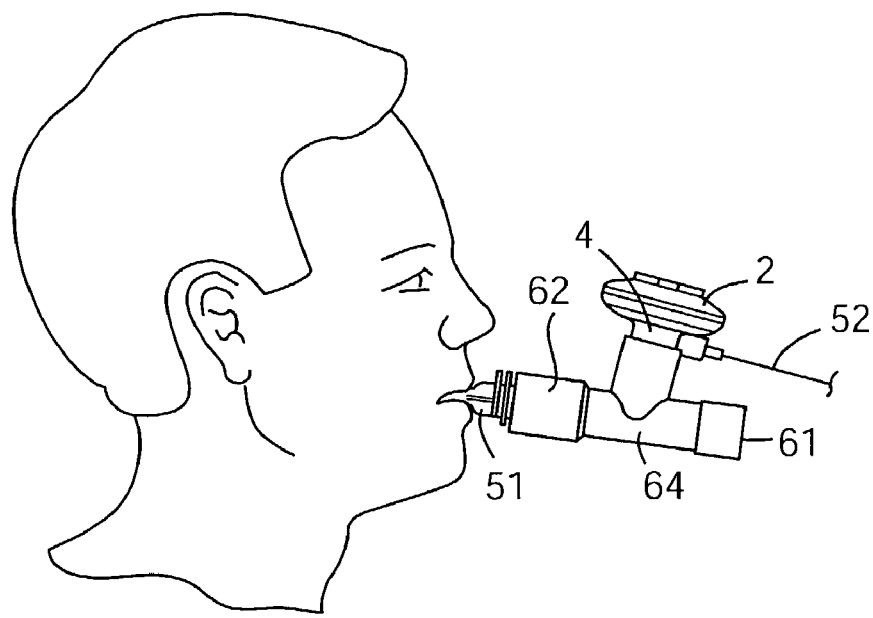
FIG. 11 is a side view of the apparatus of FIG. 9 in use mounted to a mouthpiece.
Figure 10:
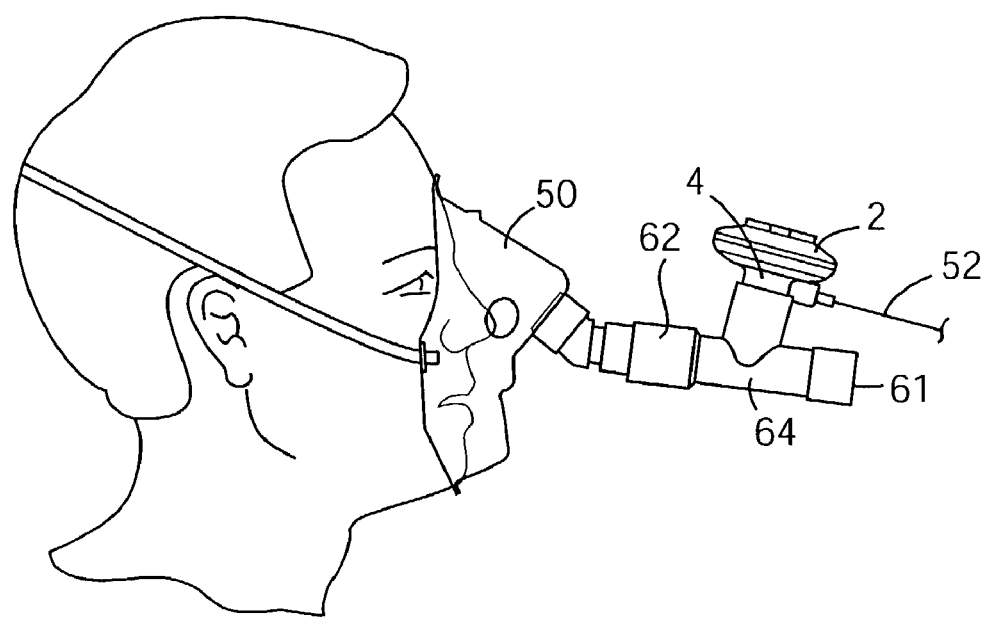
FIG. 10 is a side view of the apparatus of FIG. 9 in use mounted to a face mask.
Figure 12:
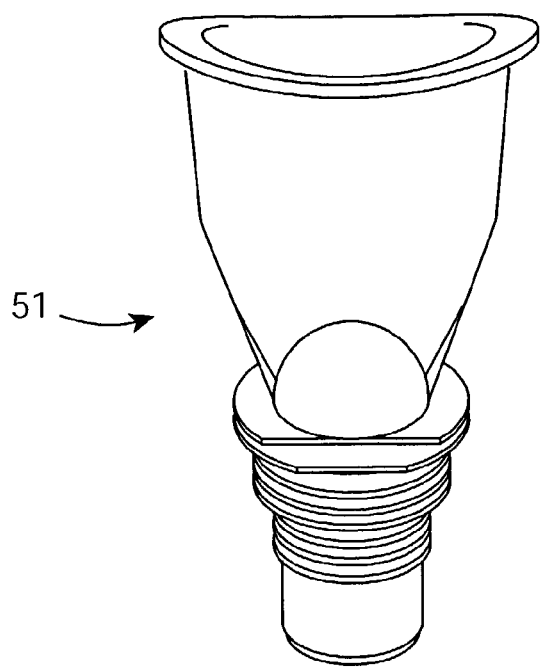
FIG. 12 is a perspective view of the mouthpiece of FIG. 11.
Figure 13:
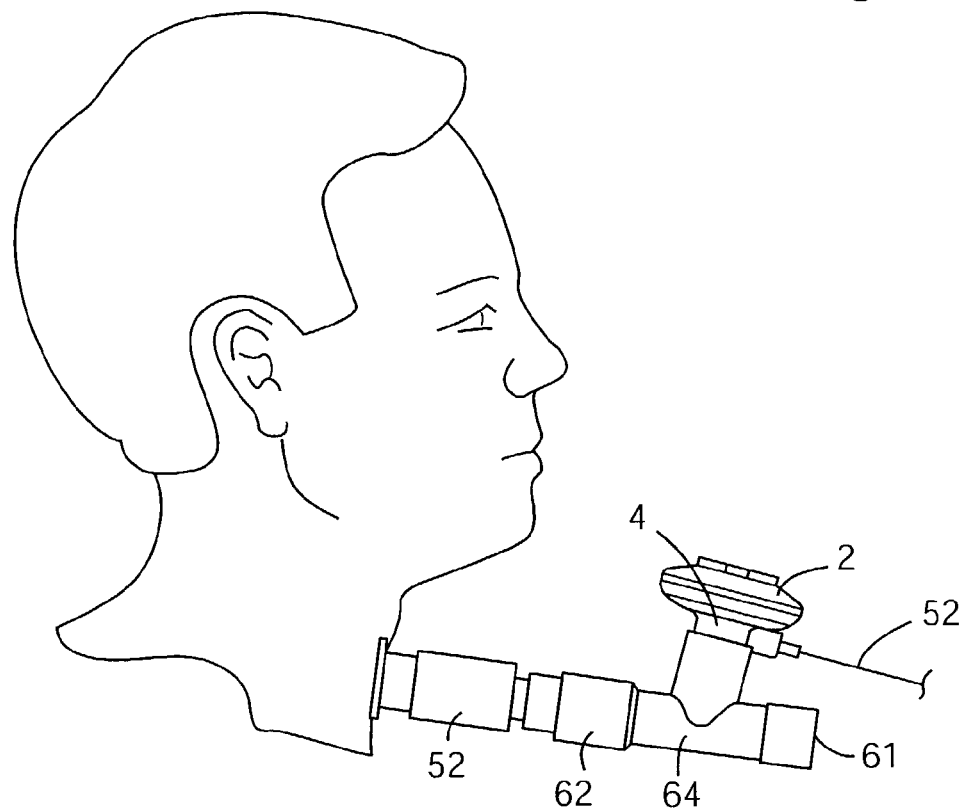
FIG. 13 is a side view of the apparatus of FIG. 9 in use mounted to an inter-tracheal tube.

A respiratory conduit, such as a face mask 50 to assist breathing of a patient (FIG. 10), or a mouthpiece 51 (FIGS. 11 and 12), or an inter-tracheal tube 52 (FIG. 13) may be provided to connect the outlet 62 of the gas conduit with the respiratory system of the patient. The respiratory conduit 50, 51, 52 may be mounted to the connector 64 at the outlet 62 of the gas conduit in a releasable manner, for example by means of an interference fit between the respiratory conduit 50, 51, 52 and the outlet 62 of the gas conduit (FIGS. 10, 11, 13).

The apparatus 1 is lightweight. By mounting the apparatus 1 to the face mask 50 which may be worn by a patient, the apparatus 1 may be used during movement of the patient. During such movement, the apparatus 1 is supported by the face mask 50 due to the interference fit between the face mask 50 and the outlet 62 of the gas conduit, the face mask 50 being in turn held in place on the patient by means of straps.

The delivery path between the aerosol generator 3 and the respiratory system of the patient may be 500 mm or shorter, for example approximately 300 mm. No baffles or flow disrupters are provided along the delivery path.

Figure 14:
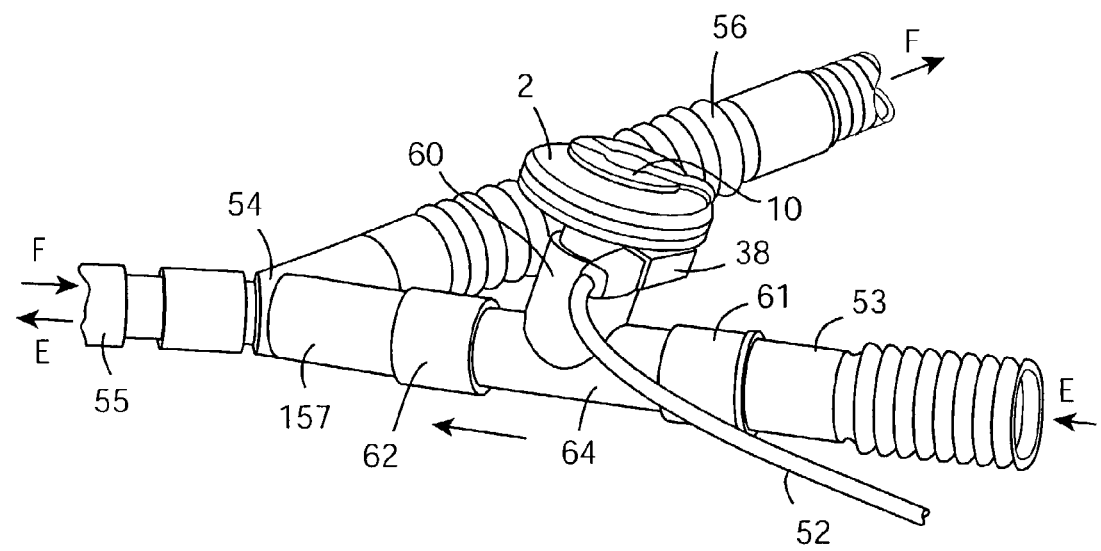
FIG. 14 is a perspective view of the apparatus of FIG. 9 in use in a breathing circuit.

A ventilator conduit 53 (FIG. 14) may be provided to connect a ventilator to the inlet 61 of the gas conduit. The ventilator conduit 53 may be mounted to the connector 64 at the inlet 61 of the gas conduit in a releasable manner, for example by means of an interference fit between the ventilator conduit 53 and the inlet 61 of the gas conduit (FIG. 14). The ventilator can be used to pump air, or oxygen, or any other suitable gas or gas mixture into the inlet 61 of the gas conduit.

FIG. 14 illustrates the assembled apparatus 1 of the invention with the ventilator conduit 53 mounted to the inlet 61 of the gas conduit, and the respiratory conduit mounted to the outlet 62 of the gas conduit. The respiratory conduit includes a Y-shaped section 54 which separates into a first arm 55 for inhalation to the respiratory system of the patient (Flow E) and a second arm 56 for exhalation from the respiratory system (Flow F).

It will be appreciated that any of the face mask 50, or the mouthpiece 51, or the inter-tracheal tube 52 may be provided between the first arm 55 and the respiratory system.

In use, a ventilator pumps a gas, such as air, through the ventilator conduit 53 into the inlet 61 of the gas conduit (Flow E). The generated aerosol of medicament passes from the aerosol generator 3 through the neck 30 of the aerosol generator housing 4, which lines the aerosol supply conduit 60 of the connector 64, and into the gas conduit of the connector 64. The aerosolized medicament is entrained with the air in the gas conduit, and the entrained mixture passes out of the gas conduit through the outlet 62 and into an inlet tube 157 of the Y-shaped section 54. The entrained mixture then passes through the first arm 55 to the respiratory system of the patient (Flow E). Upon exhalation, the exhaled gases pass from the respiratory system through the first arm 55, on through the second arm 56 to the atmosphere (Flow F).

It will further be appreciated that the Y-shaped section 54 may be provided upstream of the apparatus 1 in the ventilator circuit.

Figure 15:
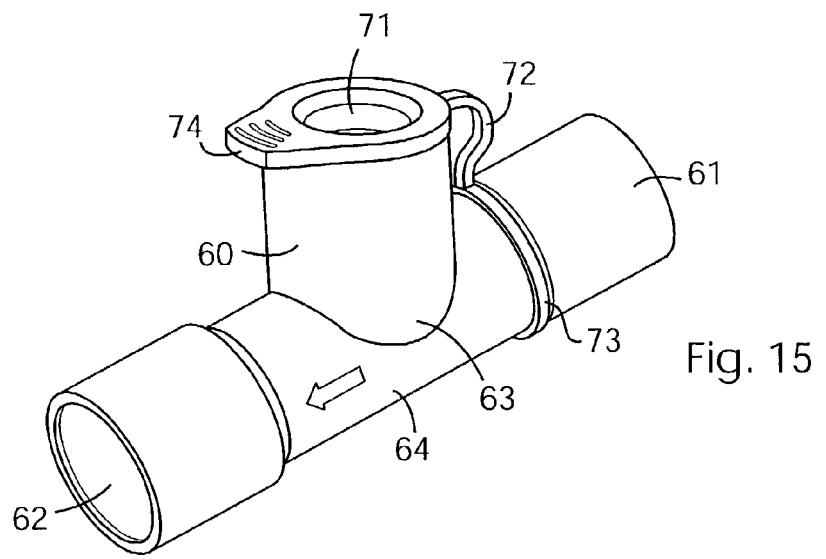
FIG. 15 is a perspective view of the connector of FIG. 8 with a cap sealing an aerosol supply conduit of the connector.
Figure 16:
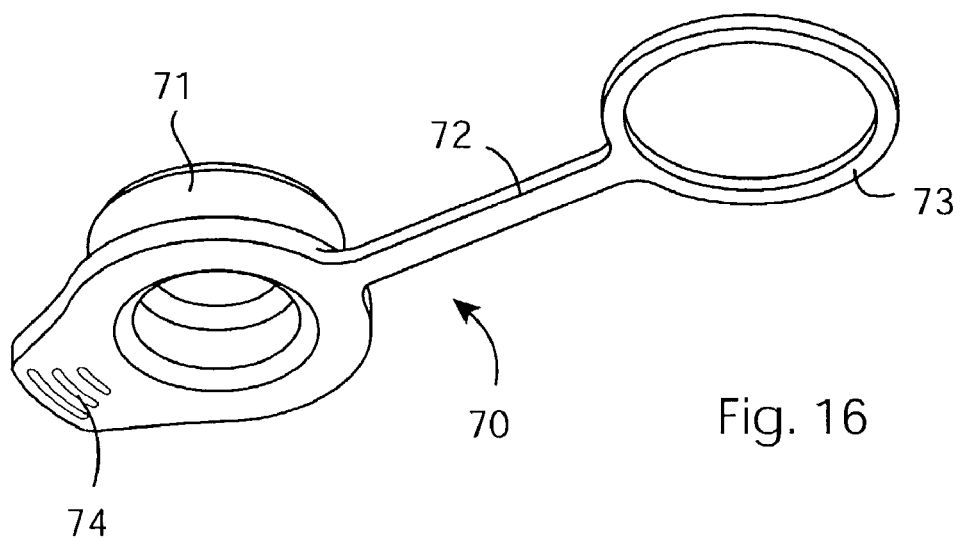
FIG. 16 is a perspective view of the cap of FIG. 15.

A capping device 70 may be provided for the connector 64 to selectively seal the aerosol supply conduit 60, as illustrated in FIGS. 15 and 16. In this case, the capping device 70 comprises an insertion plug 71 connected to a mounting ring 73 by an arm 72. The ring 73 is usually mounted around the gas conduit (FIG. 15).

The capping device 70 may be used to seal the aerosol supply conduit 60 by inserting the plug 71 into the aerosol supply conduit 60 when the aerosol generator housing 4 is dismounted from the connector 64, as illustrated in FIG. 15. By sealing the aerosol supply conduit 60, this ensures that the pressure in the gas conduit is maintained when the aerosol generator housing 4 has been dismounted. This is particularly advantageous when the connector 64 is connected in position in a ventilator circuit, as illustrated in FIG. 14, in which case the pressure in the ventilator circuit will be maintained by the capping device 70 when the aerosol generator housing 4 has been dismounted from the connector 64.

A tab 74 on the plug 71 enables ease of removal of the plug 71 from within the aerosol supply conduit 60.

When not in use, the capping device 70 may simply hang from the ring 73 mounted around the gas conduit.

Figure 17:
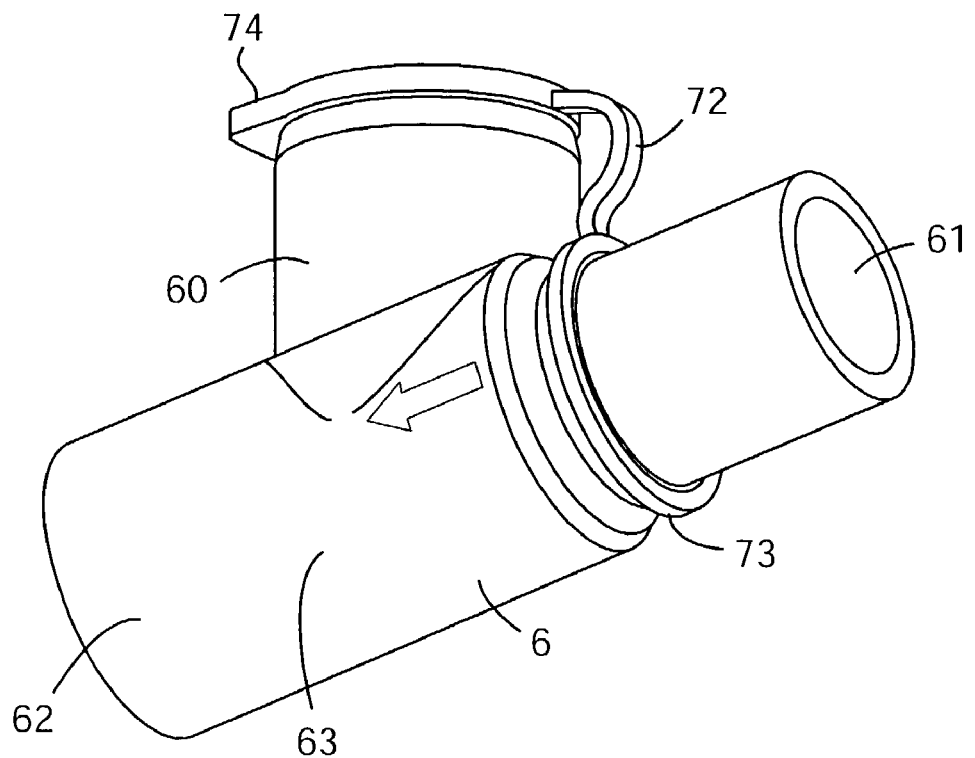
FIG. 17 is a perspective view of the connector of the apparatus of FIGS. 1 and 2 with the cap of FIG. 16 sealing an aerosol supply conduit of the connector.

The capping device 70 is also suitable for use with the connector 6, as illustrated in FIG. 17.

It will further be appreciated that the capping device 70 may be used to seal any suitable part of a pressure circuit.

Figure 17A:
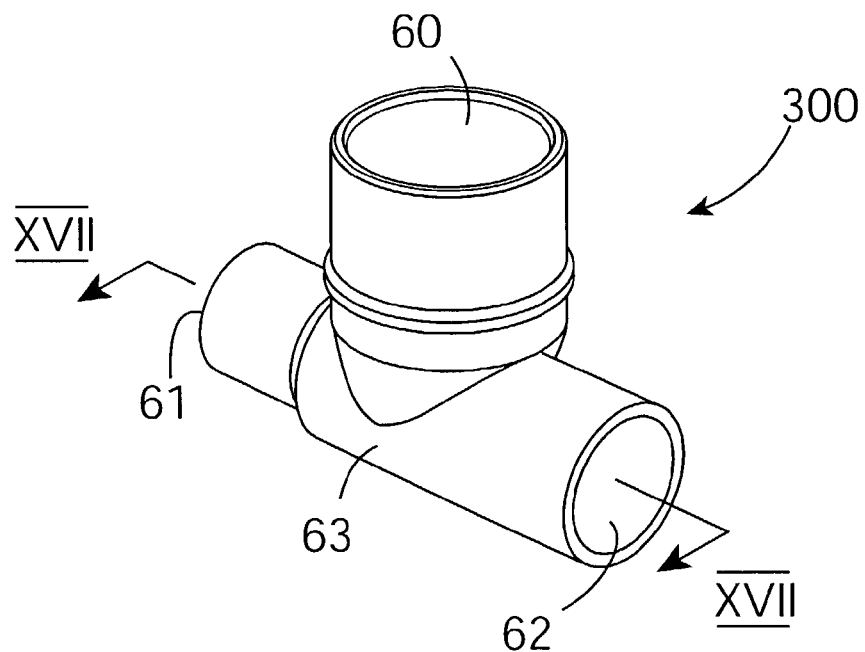
FIG. 17(a) is a perspective view of another alternative connector of the apparatus of FIGS. 1 and 2.
Figure 17B:
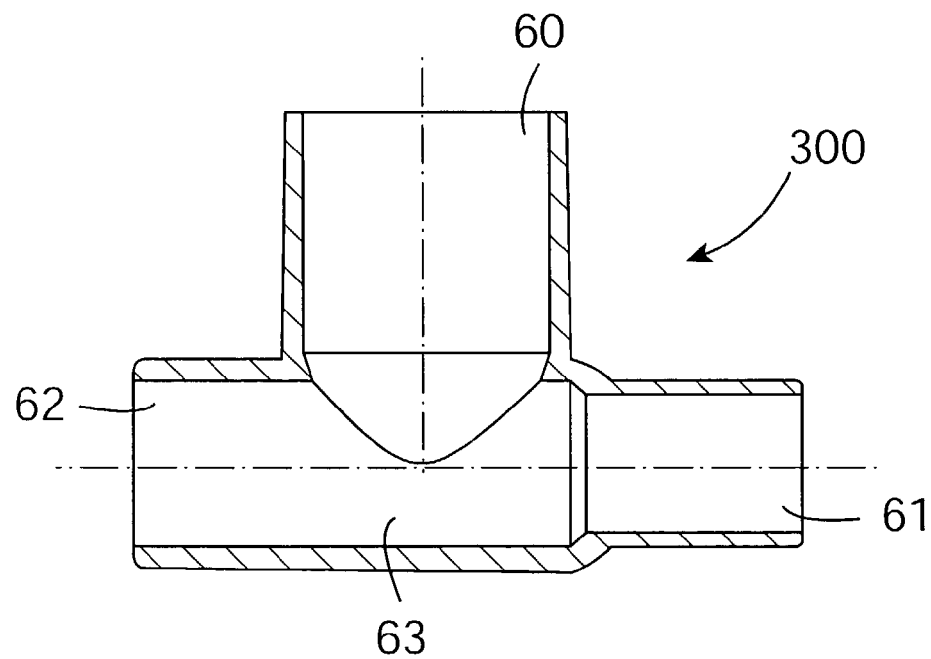
FIG. 17(b) is a cross-sectional view along line XVII-XVII in FIG. 17(a)
Figure 17C:
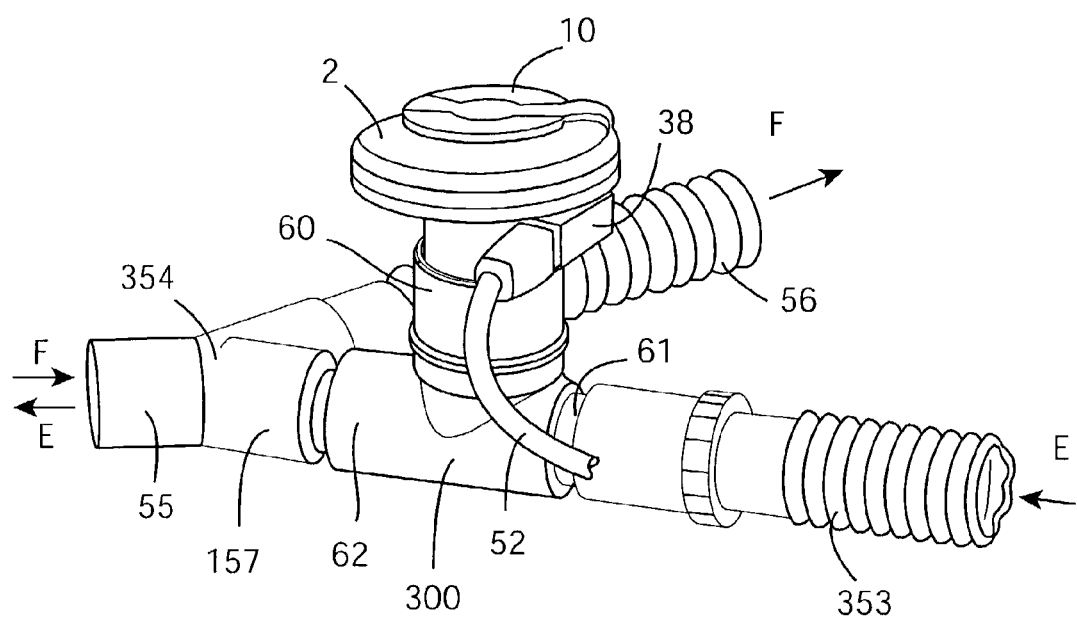
FIG. 17(c) is a perspective view of the connector of FIG. 17(a) in a breathing circuit.
Figure 17D:
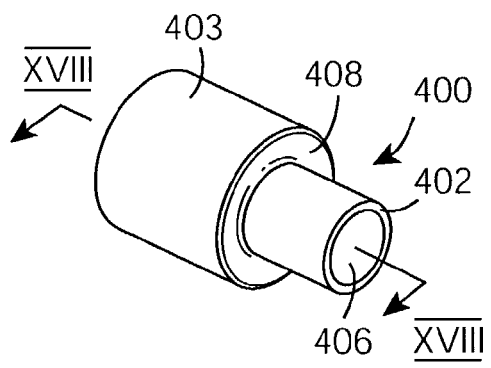
FIG. 17(d) is a perspective view of an upstream intermediate connector of the apparatus of the invention.
Figure 17E:
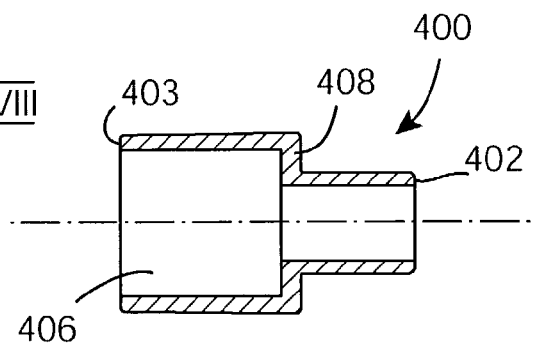
FIG. 17(e) is a cross-sectional view along line XVIII-XVIII in FIG. 17(d)
Figure 17G:
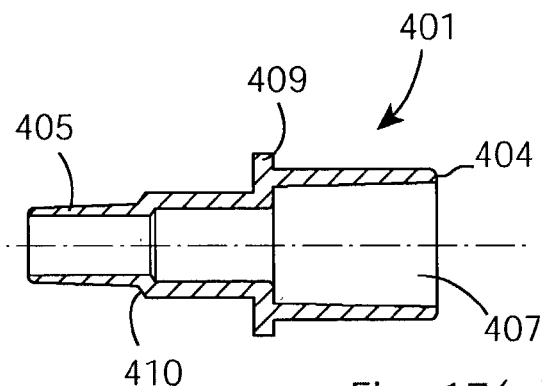
FIG. 17(g) is a cross-sectional view along line XIX-XIX in FIG. 17(f)
Figure 17F:
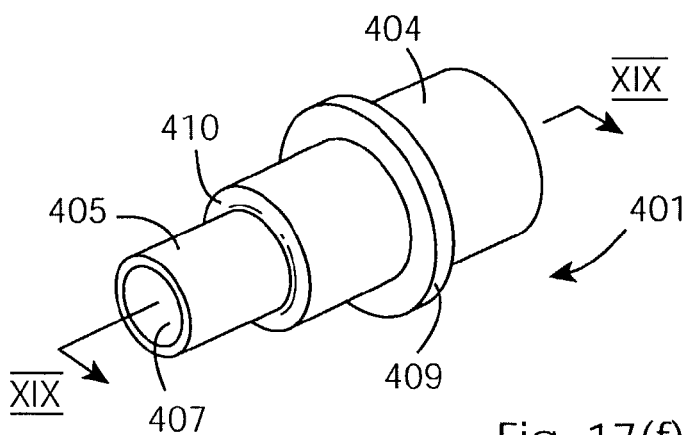
FIG. 17(f) is a perspective view of a downstream intermediate connector of the apparatus of the invention.
Figure 17H:
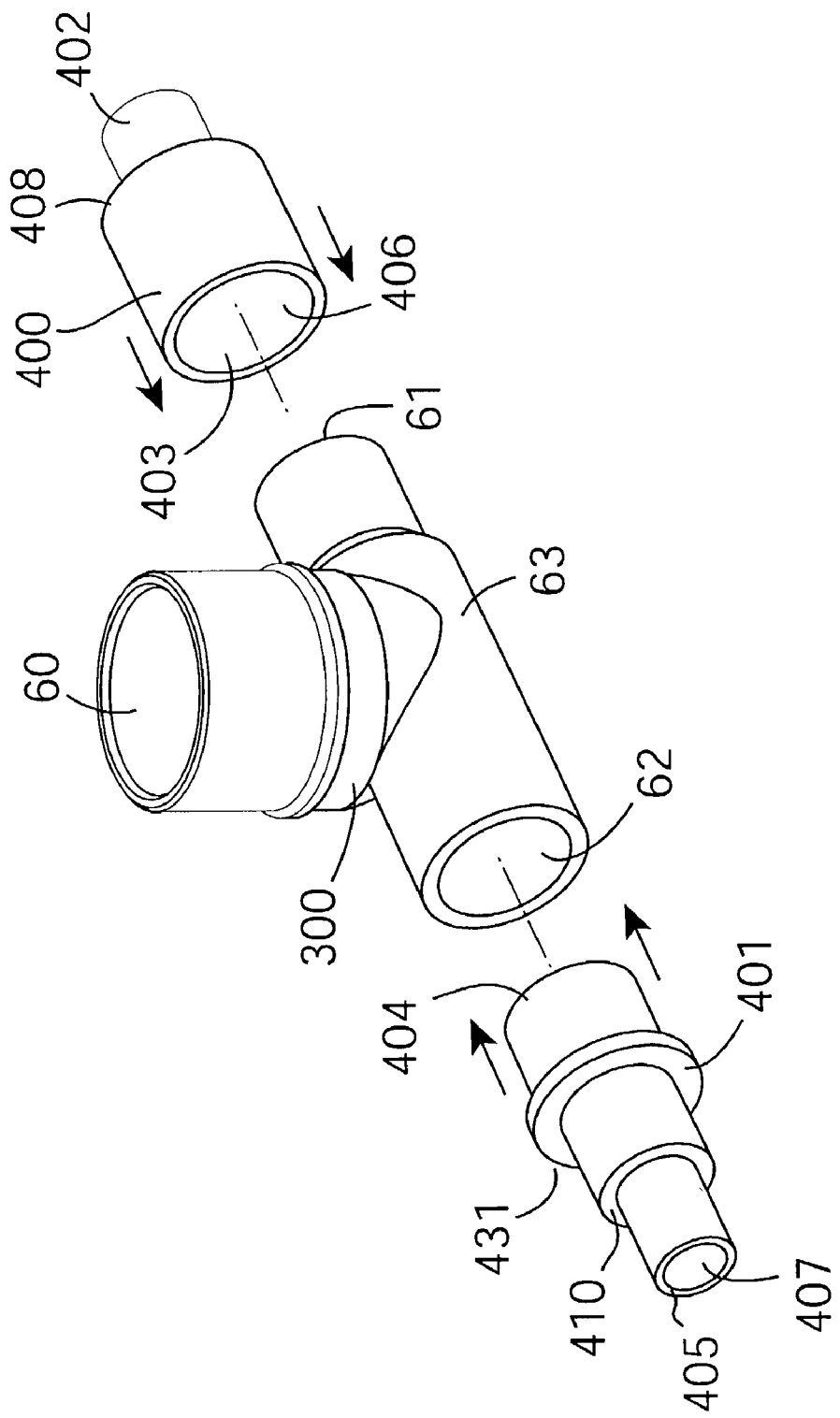
FIG. 17(h) is a perspective view illustrating mounting of the intermediate connectors of FIGS. 17(d) to 17(g) to the connector of FIG. 17(a)
Figure 17I:
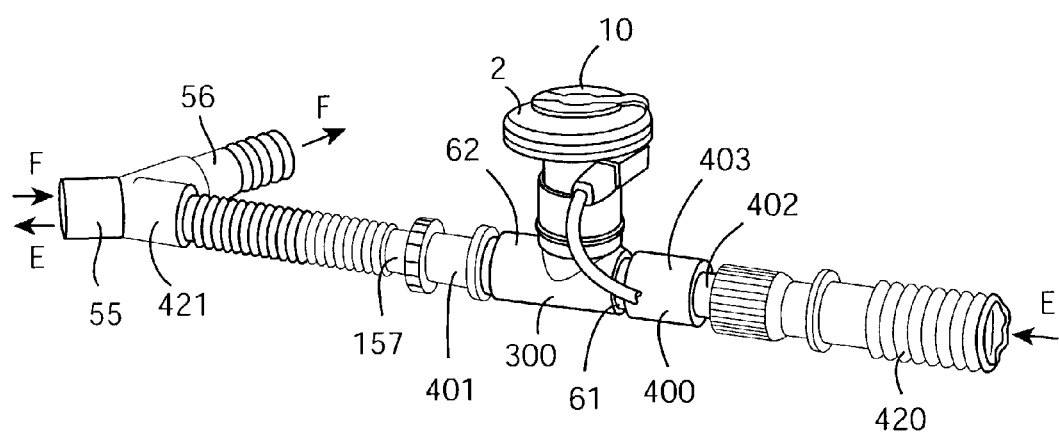
FIG. 17(i) is a perspective view of the intermediate connectors of FIGS. 17(d) to 17(g) and the connector of FIG. 17(a) in a breathing circuit.
Figure 17J:
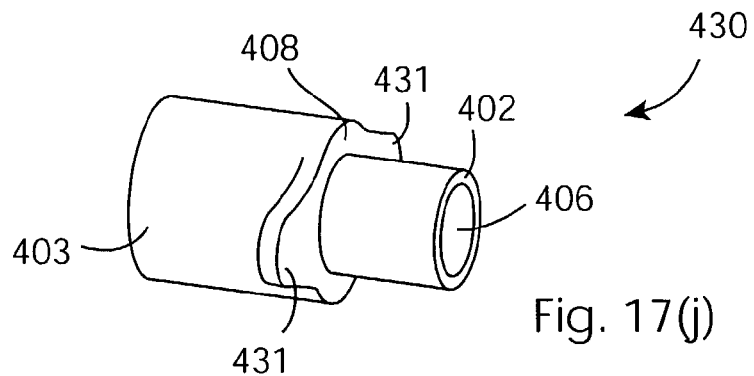
FIG. 17(j) is a perspective view of another upstream intermediate connector of the apparatus of the invention.
Figure 17K:
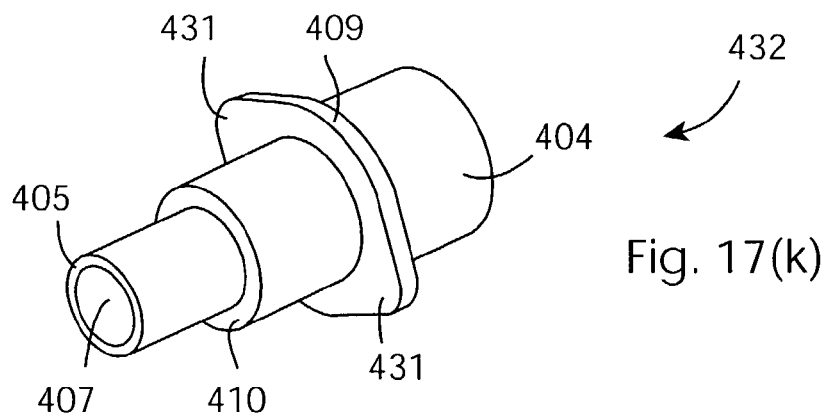
FIG. 17(k) is a perspective view of another downstream intermediate connector of the apparatus of the invention.
Figure 17M:
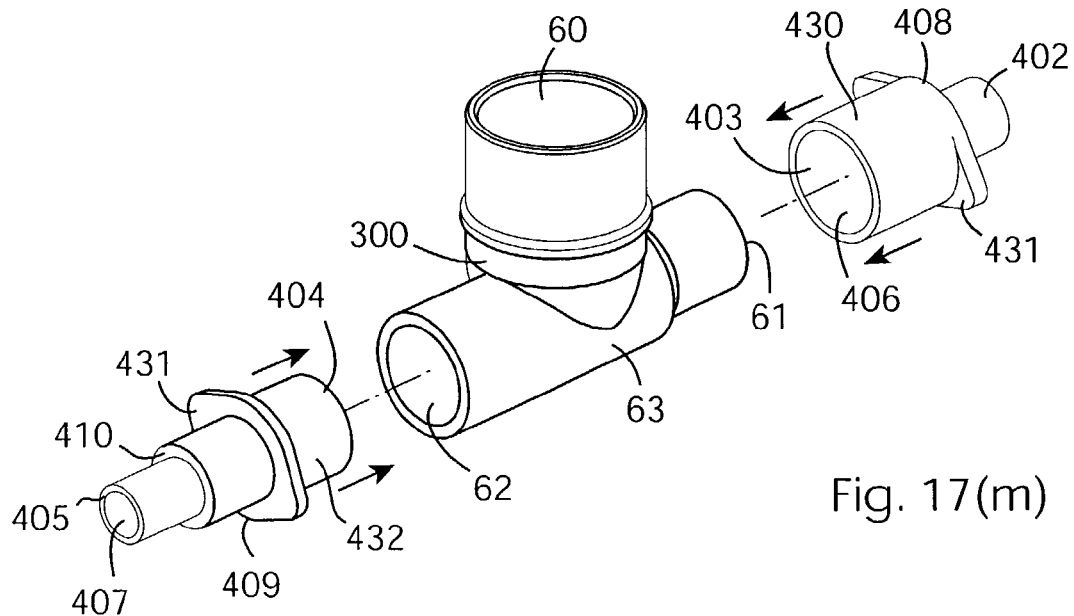
FIG. 17(m) is a perspective view illustrating mounting of the intermediate connectors of FIGS. 17(j) and 17(k) to the connector of FIG. 17(a)
Figure 18:
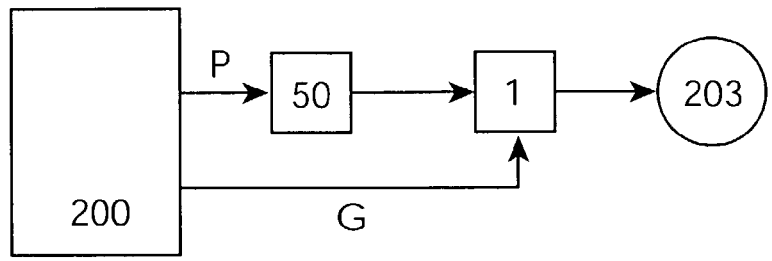
FIGS. 18 to 20 are flow diagrams illustrating operational arrangements for using the apparatus.
Figure 19:
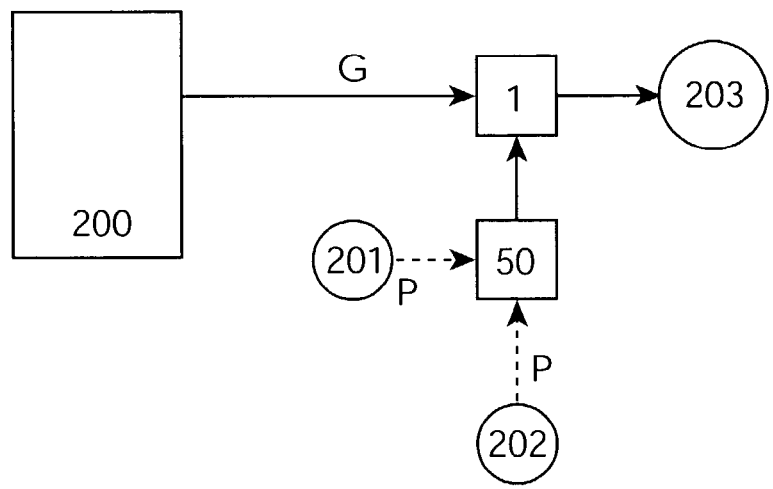
Figure 20:
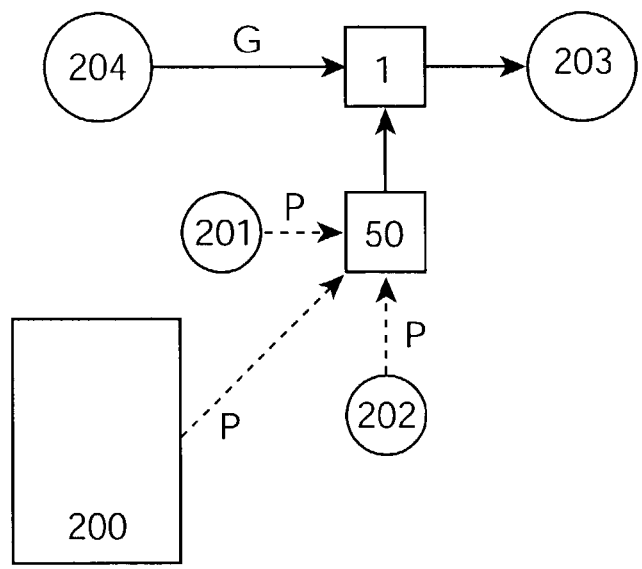

Referring now to FIGS. 17(a) to 17(c), there is illustrated another connector 300, which is similar to the connector 6 of FIGS. 1 and 2, and similar elements in FIGS. 17(a) and 17(b) are assigned the same reference numerals.

In this case, the aerosol supply conduit 60 is substantially perpendicular to the gas conduit, the aerosol supply conduit 60 subtending an angle of approximately 90° with the inlet 61 of the gas conduit (FIG. 17(b)).

In addition, the gas conduit of the connector 300 has a substantially smaller diameter, for example approximately 15 mm, than the gas conduit of the connector 6 of FIGS. 1 and 2. The connector 300 is thus particularly suitable for use in a pediatric care application. The diameter of the aerosol supply conduit 60 is the same for both the connector 300 and the connector 6 of FIGS. 1 and 2. A suitable diameter for the aerosol supply conduit 60 may be, as an example, approximately 22 mm.

FIG. 17(c) illustrates the apparatus of the invention with a small diameter pediatric ventilator conduit 353 releasably mounted to the connector 300 at the inlet 61 of the gas conduit by means of an interference fit between the male ventilator conduit 353 and the female inlet part 61. A small diameter pediatric Y-shaped respiratory section 354 is releasably mounted to the connector 300 at the outlet 62 of the gas conduit by means of an interference fit between the female inlet tube 157 of the Y-shaped section 354 and the male outlet part 62. The Y-shaped section 354 separates into a first arm 55 for inhalation to the respiratory system of the patient (Flow E) and a second arm 56 for exhalation from the respiratory system (Flow F).

The pediatric apparatus of FIG. 17(*c*) operates in a manner similar to that described previously with reference to FIG. 14.

FIGS. 17(*d*) and 17(*e*) illustrate an upstream intermediate connector 400 having an upstream end 402 and a downstream end 403. A lumen 406 extends through the intermediate connector 400 from the upstream end 402 to the downstream end 403. As illustrated in FIG. 17(*e*), the cross-sectional area of the lumen 406 increases along the length of the intermediate connector 400 from the upstream end 402 to the downstream end 403 in a discontinuous fashion at an elbow 408.

In FIGS. 17(*f*) and 17(*g*) there is illustrated a downstream intermediate connector 401 having an upstream end 404 and a downstream end 405. A lumen 407 extends through the intermediate connector 401 from the upstream end 404 to the downstream end 405. As illustrated in FIG. 17(*g*), the cross-sectional area of the lumen 407 decreases along the length of the intermediate connector 401 from the upstream end 404 to the downstream end 405 in a discontinuous fashion at two elbows 409, 410.

The upstream intermediate connector 400 may be releasably mounted to the inlet 61 of the gas conduit of the connector 300 by means of an interference fit between the female inlet part 61 and the male downstream end 403 of the intermediate connector 400 (FIG. 17(*h*)). Similarly the downstream intermediate connector 401 may be releasably mounted to the outlet 62 of the gas conduit of the connector 300 by means of an interference fit between the female upstream end 404 of the intermediate connector 401 and the male outlet part 62 (FIG. 17(*h*)).

As illustrated in FIG. 17(*i*), a very small diameter, for example approximately 7.5 mm, neo-natal ventilator conduit 420 may then be releasably mounted to the upstream end 402 of the upstream intermediate connector 400 by means of an interference fit between the female upstream end 402 of the upstream intermediate connector 400 and the male ventilator conduit 420. Similarly a very small diameter, for example approximately 7.5 mm, neo-natal bifurcated, i.e. Y-shaped, respiratory section 421 may be releasably mounted to the downstream end 405 of the downstream intermediate connector 401 by means of an interference fit between the male inlet tube 157 of the Y-shaped section 421 and the female downstream end 405 of the downstream intermediate connector 401.

In this manner, the intermediate connectors 400, 401 may be used to facilitate assembly of the connector 300 within a neo-natal breathing circuit, as illustrated in FIG. 17(*i*). In particular, the upstream intermediate connector 400 provides a step-up in the cross-sectional area of the flow from the smaller diameter neo-natal ventilator conduit 420 to the larger diameter gas conduit of the connector 300. Also the downstream intermediate connector 401 provides a step-down in the cross-sectional area of the flow from the larger diameter gas conduit of the connector 300 to the smaller diameter neo-natal Y-shaped respiratory section 421.

The Y-shaped section 421 separates into a first arm 55 for inhalation to the respiratory system of the patient (Flow E) and a second arm 56 for exhalation from the respiratory system (Flow F). Operation of the neo-natal apparatus of FIG. 17(*i*) operates in a manner similar to that described previously with reference to FIG. 14.

It is to be noted that the intermediate connectors 400, 401 provide a bridging means between the connector 300 and the ventilator conduit 420 and the Y-shaped section 421, so that a single connector 300 may be used for both pediatric care applications (FIG. 17(*c*)) and neo-natal care applications (FIG. 17(*i*)).

The upstream intermediate connector 430 of FIG. 17(*j*) has two diametrically opposed protruding flanges 431 on the elbow 408 of the intermediate connector 430. Similarly the downstream intermediate connector 432 of FIG. 17(*k*) has two diametrically opposed protruding flanges 431 on the elbow 409 of the intermediate connector 432.

The flanges 431 provide a handle means for gripping the intermediate connectors 430, 432 to assist mounting and demounting of the intermediate connectors 430, 432 to the connector 300, as illustrated in FIG. 17(*m*). This feature may be applied to any of the connectors.

Referring now to FIGS. 18 to 20, there are illustrated some possible arrangements for using the apparatus 1, according to the invention, for delivering medicament to a respiratory system 203 of a patient.

In the arrangement of FIG. 18, gas is pumped from a ventilator 200 into the inlet 61 of the gas conduit (line G). The power source for the controller 50 which controls operation of the apparatus 1 is provided by the ventilator 200 (line P).

In the arrangement of FIG. 19, gas is pumped from the ventilator 200 into the inlet 61 of the gas conduit (line G). The power source for the controller 50 is provided by a battery 201 and/or a mains power source 202 (lines P).

In the arrangement of FIG. 20, gas is drawn into the inlet 61 of the gas conduit directly from the atmosphere 204 (line G). The power source for the controller 50 is provided by the battery 201 and/or the mains power source 202 and/or the ventilator 200 (lines P).

In the case where the power source is provided by the battery 201, and the inlet 61 is open to the atmosphere 204, the apparatus 1 is highly mobile. In particular, the apparatus 1 may be worn or held by the patient as the patient takes exercise.

Figure 22:
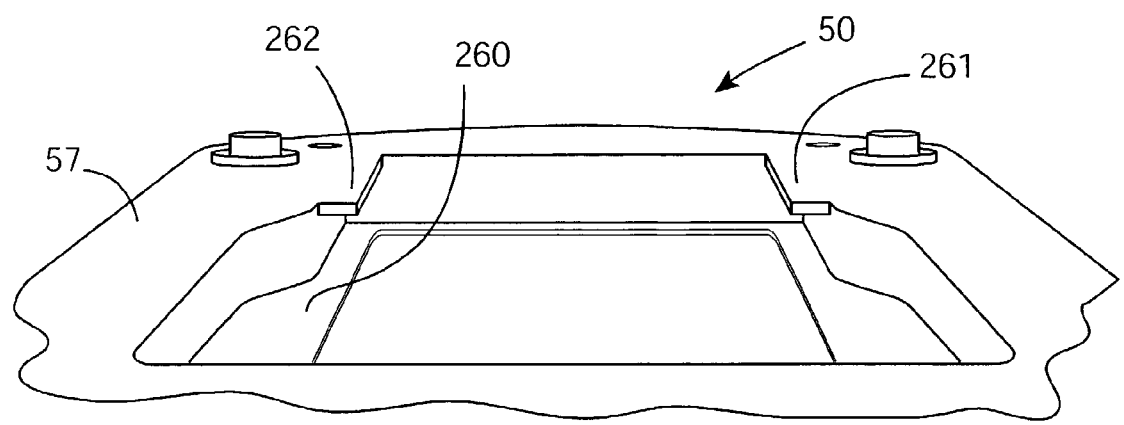
FIG. 22 is a perspective view along the rear side of the controller of FIG. 21.
Figure 21:
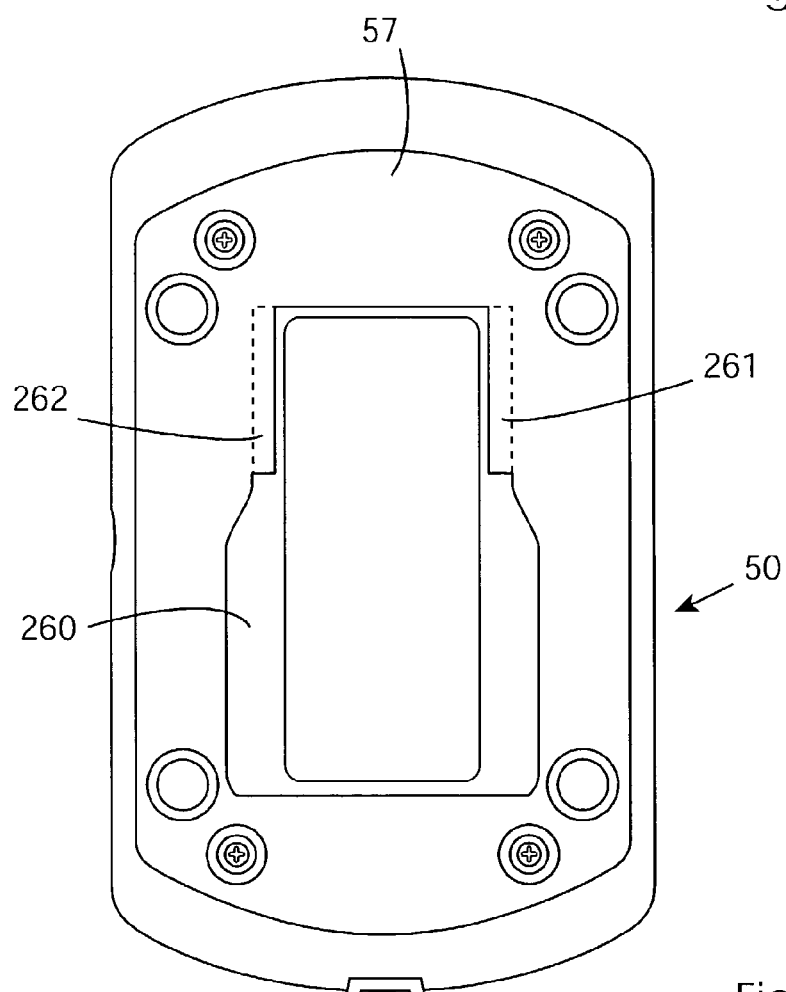
FIG. 21 is a plan view of a rear side of the controller of FIG. 7.

FIG. 21 illustrates a rear side of the controller housing 57. The housing 57 defines a recess 260 in the rear side of the housing 57, and two opposed ledges 261, 262 which overhang partially over recess 260, as illustrated most clearly in FIG. 22.

Figure 23:
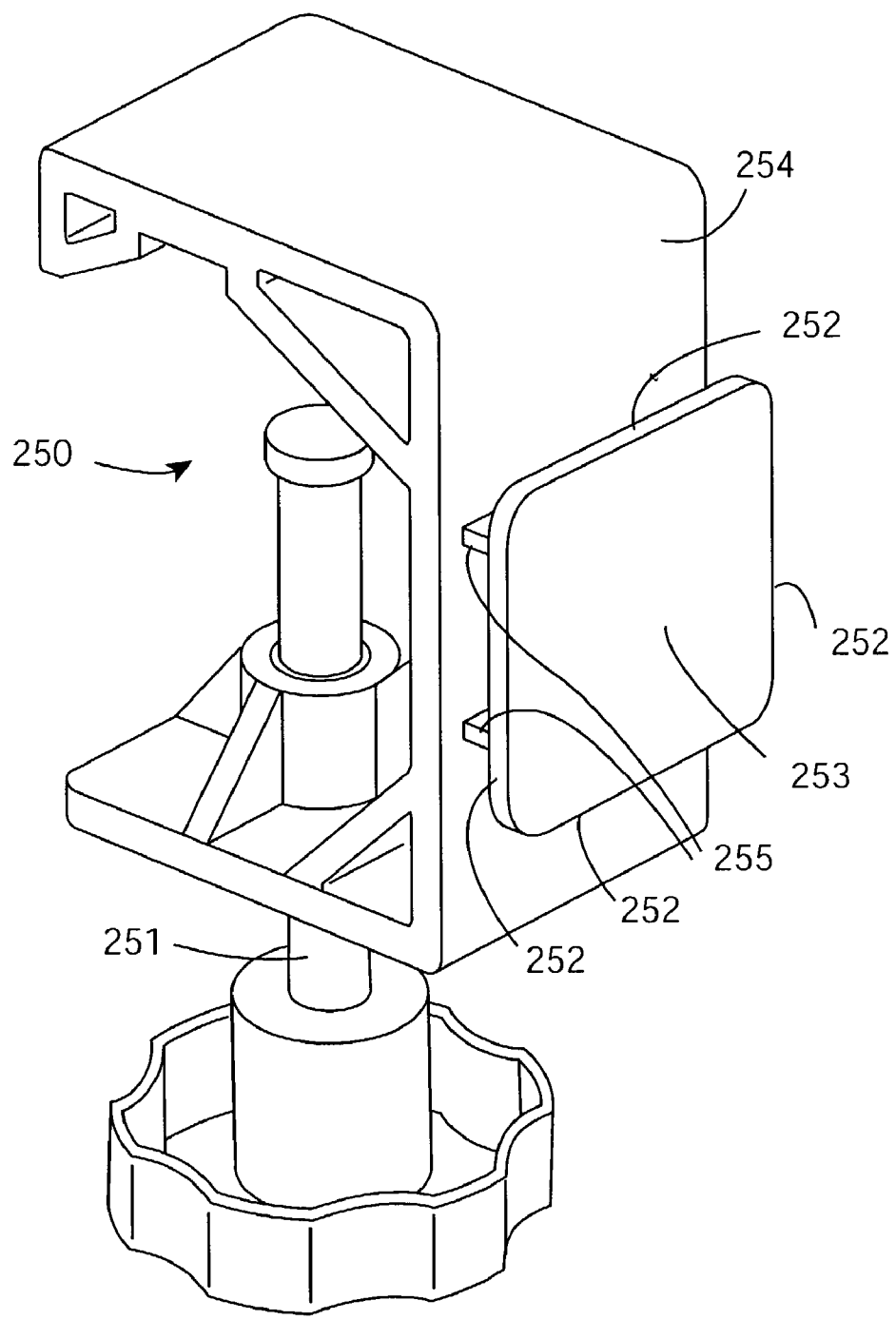
FIG. 23 is a perspective view of a mounting device.

Referring now to FIG. 23, there is illustrated a mounting device 250. The mounting device 250 comprises means for attaching the device 250 to a support, such as an intravenous (IV) pole or a medi-rail, and hook means for supporting a medical device, such as the controller housing 57.

The attachment means is provided, in this case, by a releasable clamp 251. The attachment means may alternatively be provided by a clip, such as a belt-clip.

The hook means is configured to define a plurality of in this case four, support surfaces 252 for supporting the housing 57 in an upright configuration. The support surfaces 252 are provided by a lip 253 which protrudes from a main body 254 of the mounting device 250. The lip 253 is spaced from the main body 254 by two legs 255 (FIG. 23).

Figure 24:
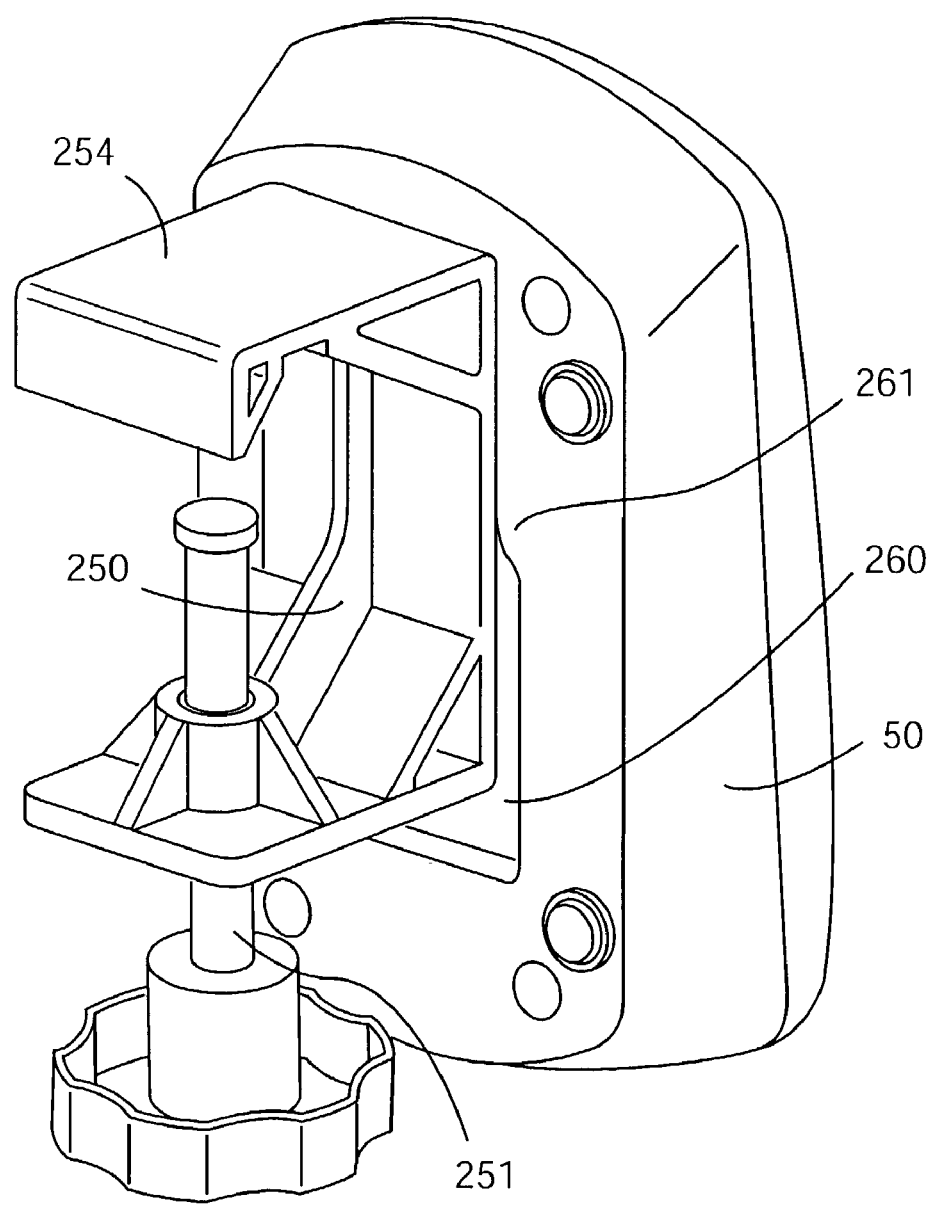
FIGS. 24 and 25 are perspective views of the mounting device of FIG. 23 supporting the controller of FIG. 21.
Figure 25:
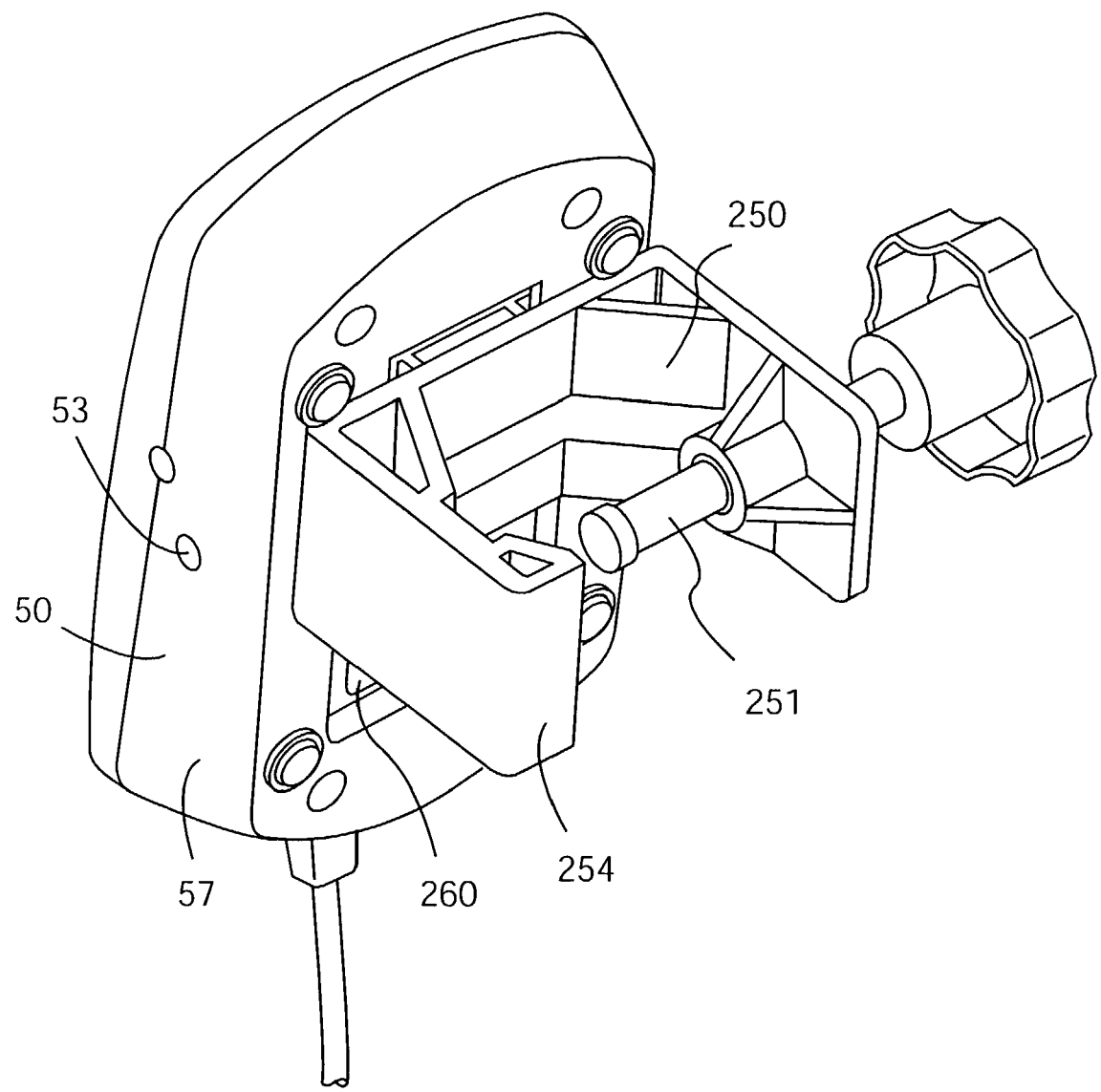

In this case, the mounting device 250 is used to support the controller housing 57, as illustrated in FIGS. 24 and 25. The lip 253 of the mounting device 250 may be inserted into the wider end of the recess 260 in the rear side of the controller housing 57 and then slid along the recess 260 until the lip 253 is partially enclosed behind the ledges 261, 262. In this configuration, the controller housing 57 is releasably supported by the mounting device 250 (FIGS. 24 and 25).

The lip 253 comprises a plurality of support surfaces 252. This arrangement enables the controller housing 57, or any other suitable medical device, to be supported in an upright orientation when the mounting device 250 is clamped to a horizontal support, such as a medi-rail (FIG. 24), or when the mounting device 250 is clamped to a vertical support, such as an IV pole (FIG. 25).

It will be appreciated that the support surfaces 252 may be arranged at angles other than 90° relative to one another.

Figure 26:
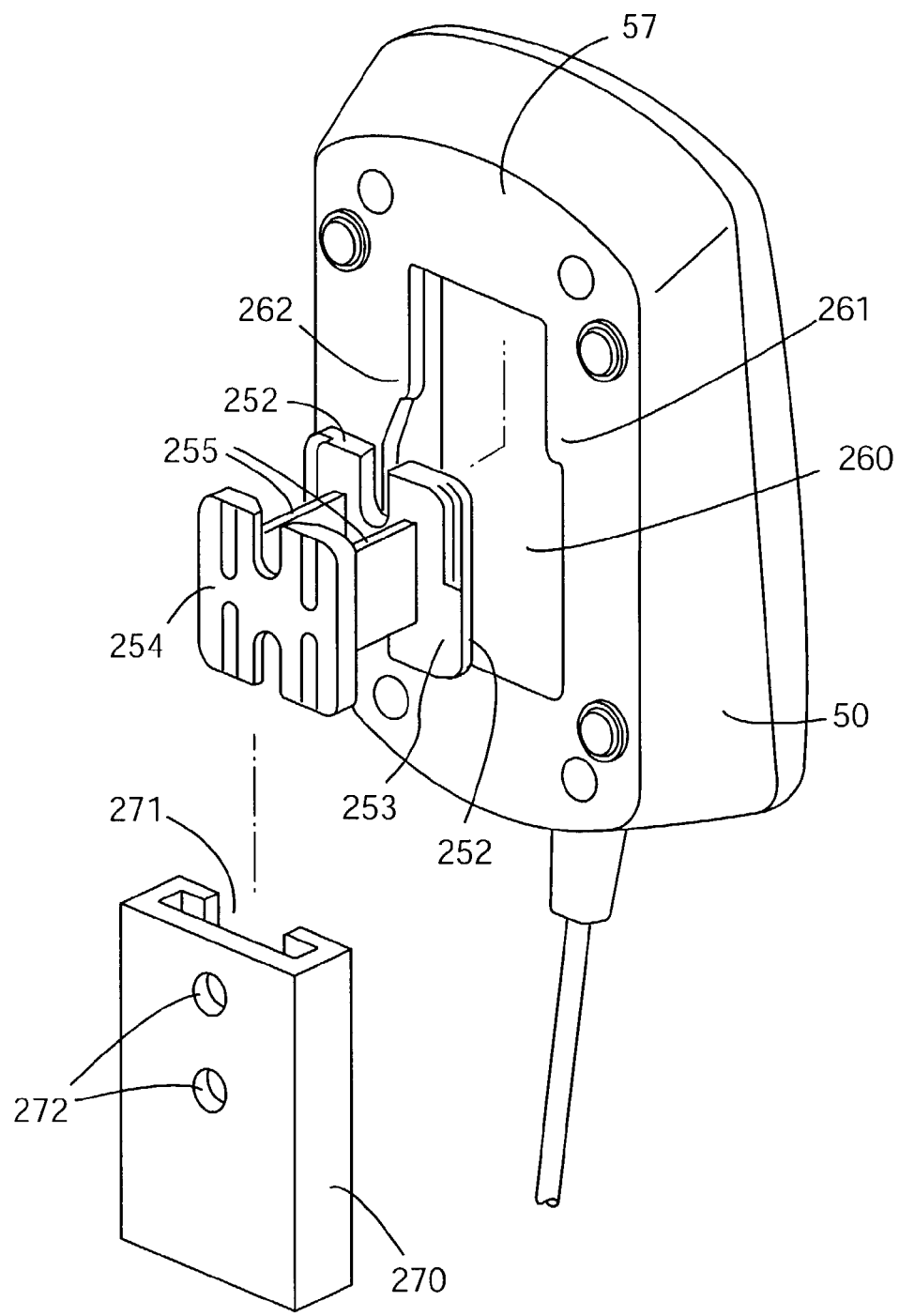
FIG. 26 is an exploded, perspective view of another mounting device in use with the controller of FIG. 21.
Figure 27:
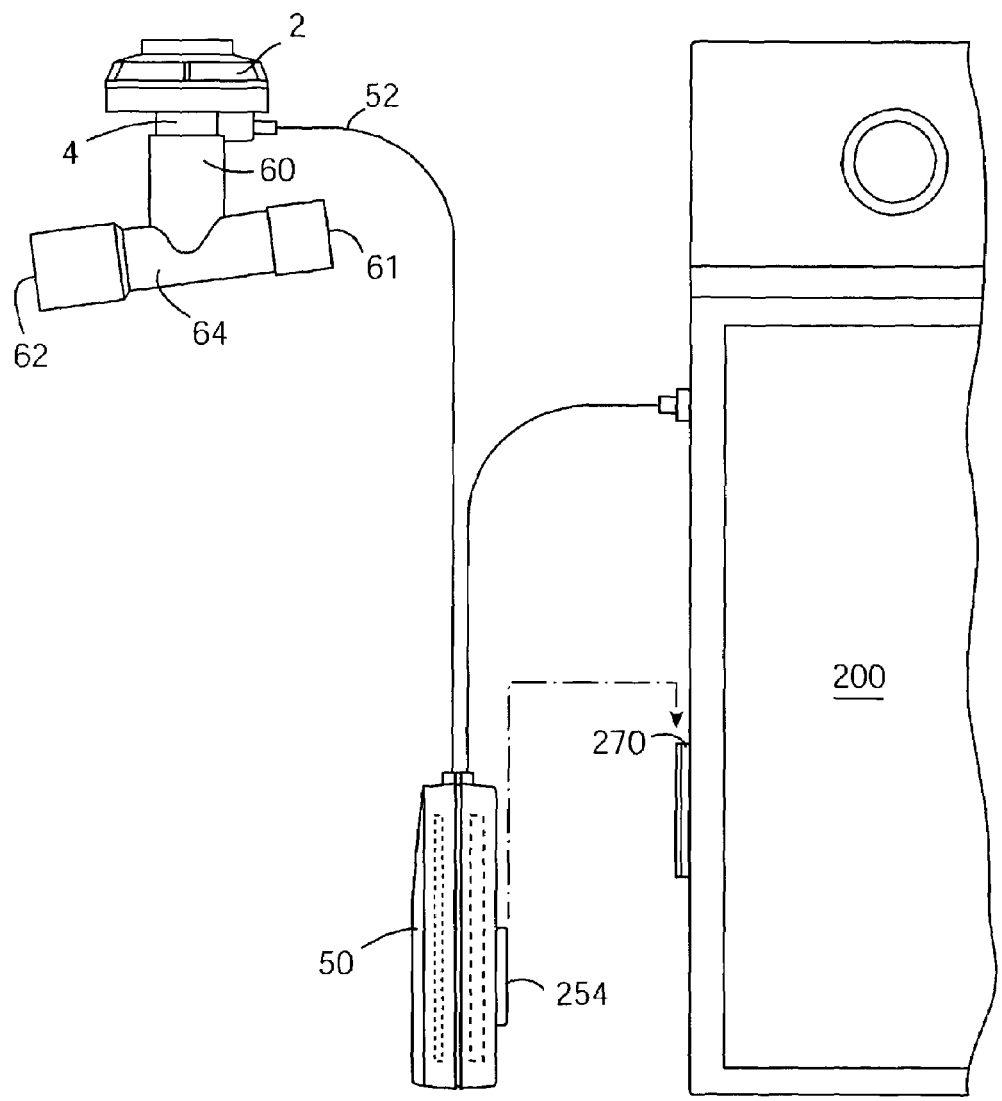
FIG. 27 is a side view of the apparatus of FIG. 9 in use with the controller of FIG. 21 and the mounting device of FIG. 26.

Referring now to FIGS. 26 and 27 there is illustrated another mounting device which is similar to the mounting device 250 of FIGS. 23 to 25, and similar elements in FIGS. 26 and 27 are assigned the same reference numerals.

In this case, the attachment means is provided by a sleeve 270 and the hook means may be moved relative to the sleeve 270 to selectively disassociate the hook means from the attachment means. The sleeve 270 defines a groove 271 in which the main body 254 may be slidably received (FIG. 26).

The sleeve 270 may be permanently or temporarily attached to a support, such as a medi-rail, or an IV pole, or a ventilator 200, as illustrated in FIG. 27, by means of fixing pins inserted through apertures 272 in sleeve 270.

Figure 28:
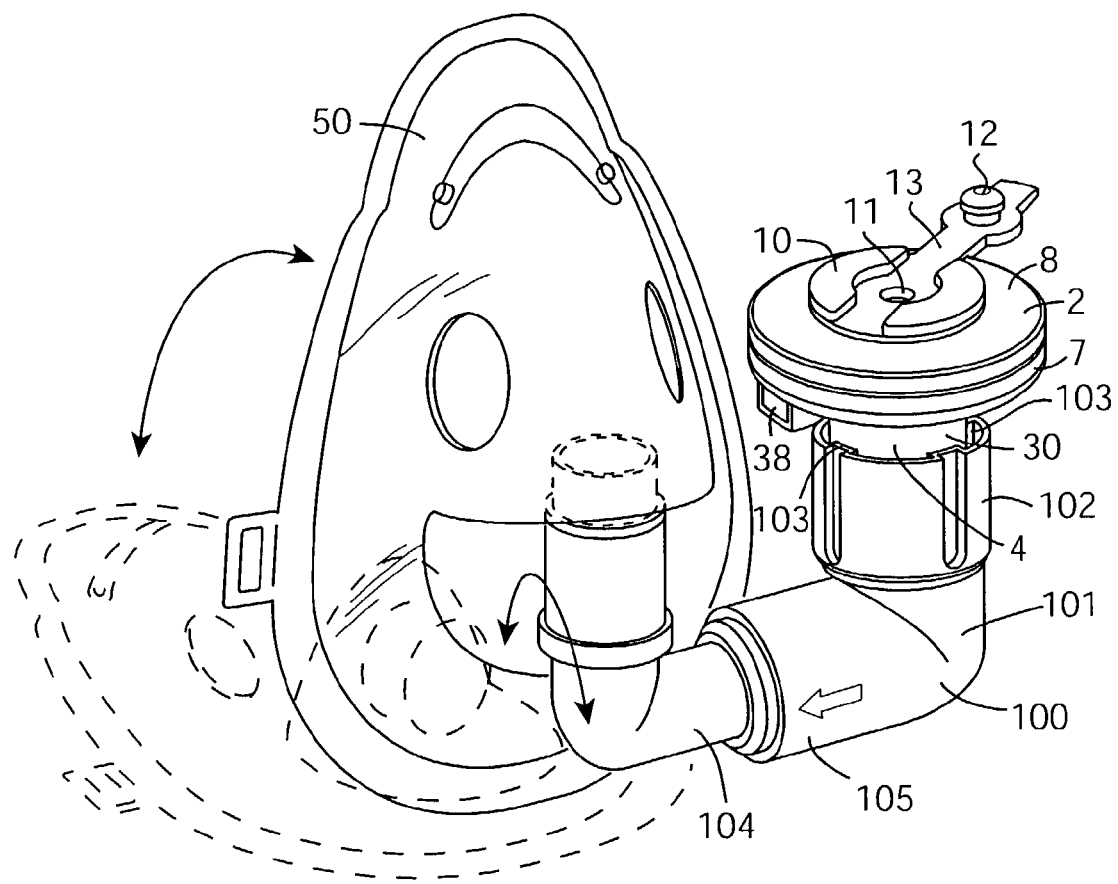
FIG. 28 is a perspective view of an apparatus for delivery of a medicament to a respiratory system according to another embodiment of the invention.
Figure 29:
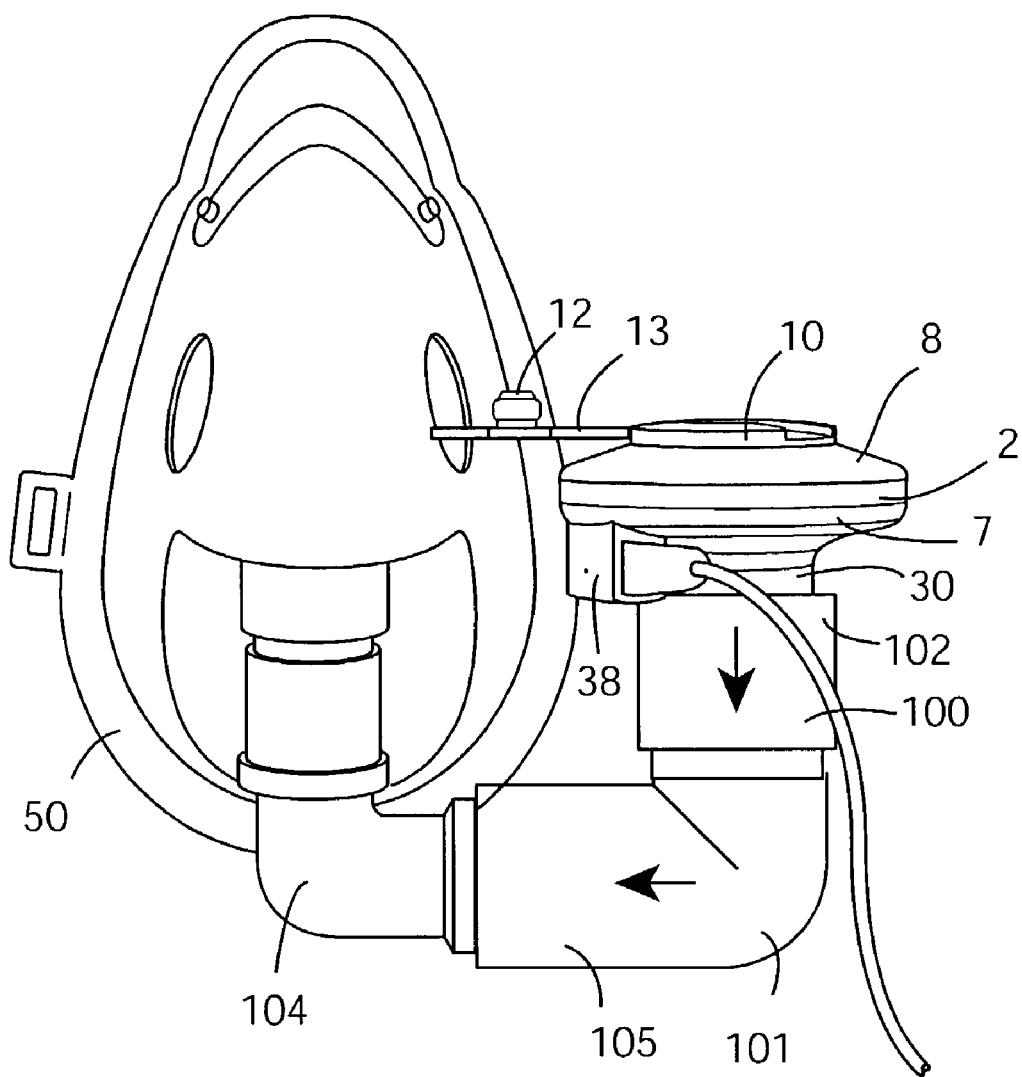
FIG. 29 is a side view of the apparatus in FIG. 28 according to another embodiment of the invention.
Figure 30:
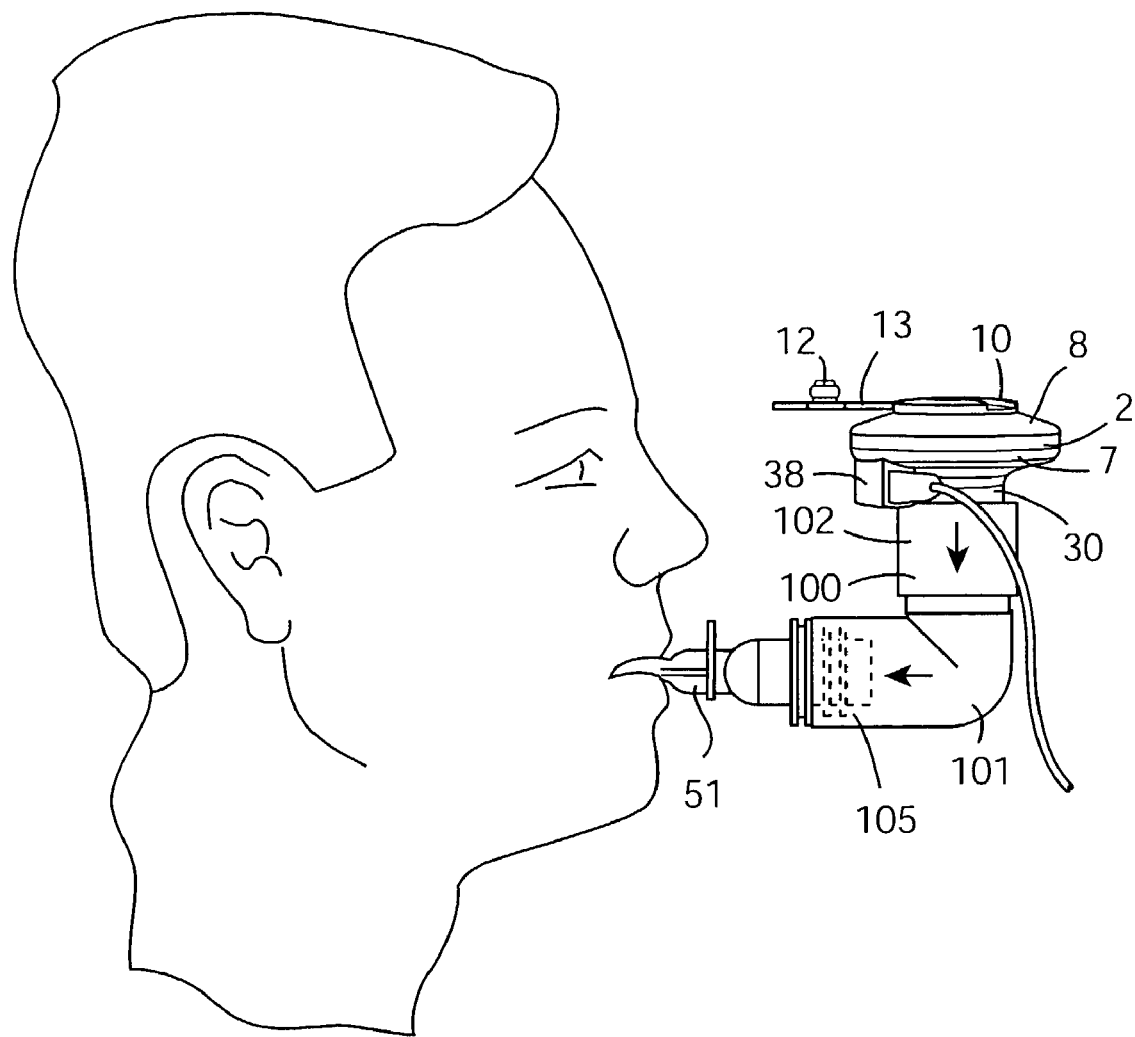
FIG. 30 is a side view of the apparatus in FIG. 28 in use according to another embodiment of the invention.

Referring to FIGS. 28 to 30, there is illustrated another apparatus 100 according to the invention, which is similar to the apparatus 1 of FIGS. 1 to 27, and similar elements in FIGS. 28 and 29 are assigned the same reference numerals.

In this case, the connector 101 is of a general L-shape. The aerosol supply conduit is defined by the neck 30 of the aerosol generator housing 4, and the inlet 102 of the gas conduit extends co-axially around the neck 30.

A plurality of inward protrusions 103 are provided on the inlet 102 of the gas conduit, spaced radially around the circumference of the inlet 102 (FIG. 28). The connector 101 is releasably mounted to the aerosol generator housing 4 by means of an interference fit between the protrusions 103 and the neck 30 of the aerosol generator housing 4.

This arrangement facilitates passage of air into the inlet 102 of the gas conduit between the protrusions 103.

An intermediate elbow portion 104 is provided to connect the face mask 50 to the outlet 105 of the gas conduit. The elbow 104 is mounted to the face mask 50 in such a manner that movement of the face mask 50 relative to the elbow 104 is possible, in particular the face mask 50 is rotatable about the elbow 104. The elbow 104 is also mounted to the outlet 105 of the gas conduit in a moveable manner, in particular rotation of the elbow 104 and the face mask 50 about the longitudinal axis of the outlet 105 of the gas conduit is possible, as illustrated in FIG. 28. This arrangement facilitates use of the face mask 50 with a patient in a sitting/standing position, or in a lying position, or in any inclined position, while maintaining the reservoir 2 and the aerosol generator housing 4 assembly in a suitable orientation that enables gravitational flow of the liquid medicament from the reservoir 2 to the aerosol generator 3.

The apparatus 100 is also suitable for use with the mouthpiece 51, as illustrated in FIG. 30, or with any other suitable respiratory conduit, such as the inter-tracheal tube 52.

The power usage of the apparatus 1 is relatively low, in this case approximately 1.5W, thus the associated heat generated during use is negligible. The apparatus 1 may therefore be placed as close to the patient as desired, even touching the patient for long periods of use without causing discomfort to the patient, or without burning the patient.

The cap 10 is mounted to the reservoir 2. Therefore, there are no loose parts which could be contaminated, broken or lost during filling or refilling of the reservoir 2.

The aerosol generator 3 produces an aerosol of medication with consistent mono-dispersed particles within a controlled range of aerosol particle sizes. No filters/baffles or flow disrupters are required between the aerosol generator and the respiratory system of the patient, and no degradation of the medication occurs as a result of the aerosol generation process.

The invention is not limited to the embodiments hereinbefore described, with reference to the accompanying drawings, which may be varied in construction and detail.

What is claimed is:

1. An apparatus for delivery of a medicament to a respiratory system, the apparatus comprising:
a reservoir for a liquid medicament for delivery to a respiratory system, the reservoir having an upper liquid medicament inlet port and a lower medicament outlet;
an aerosol generator at the medicament outlet of the reservoir for aerosolizing the liquid medicament, wherein:
the reservoir has a lower portion substantially shaped and sloped towards the aerosol generator to promote flow of the liquid medicament towards the aerosol generator at the medicament outlet by gravitational action; and
the aerosol generator comprises a vibratable member having a plurality of apertures extending between a first surface and a second surface, the first surface being adapted to receive the liquid medicament and the aerosol generator being configured to generate an aerosol at the second surface;
a connector for entraining the aerosolized medicament from the aerosol generator with a gas, the connector being releasably mounted to the reservoir, wherein the connector comprises a gas conduit having a gas-conduit inlet, a gas-conduit outlet and an aerosol supply conduit for delivering the aerosolized medicament from the aerosol generator into the gas conduit to entrain the aerosolized medicament with a gas; and a respiratory conduit connecting the outlet of the gas conduit to the respiratory system, wherein the respiratory conduit is rotatable about a longitudinal axis of the outlet of the gas conduit, whereby the reservoir may be maintained at suitable orientation that enables gravitational flow of liquid medicament from the reservoir to the aerosol generator, wherein the liquid medicament inlet port is adapted to mate with a delivery tip of a supply container, whereby liquid medicament can be delivered into the reservoir from the supply container without dismounting parts of the apparatus.

2. The apparatus recited in claim 1 wherein the inlet port is an upper inlet port and the outlet is a lower outlet for gravitational flow of the liquid medicament from the reservoir to the aerosol generator.

3. The apparatus recited in claim 2 further comprising a plug for selectively sealing the upper inlet port.

4. The apparatus recited in claim 2 wherein an interior surface of the reservoir is configured to promote flow of the liquid medicament towards the aerosol generator.

5. The apparatus recited in claim 4 wherein the interior surface of the reservoir is inclined towards the aerosol generator.

6. The apparatus recited in claim 5 wherein the reservoir defines a substantially conical shape at least in the region adjacent the aerosol generator.

7. The apparatus recited in claim 1 wherein:
the reservoir defines an access opening in a wall of the reservoir to facilitate access to an interior of the reservoir; and
the reservoir comprises a cap for mounting at the access opening.

8. The apparatus recited in claim 7 wherein the inlet port is provided through the cap.

9. The apparatus recited in claim 1 wherein the aerosol supply conduit subtends an angle of less than 90° with the inlet of the gas conduit.

10. The apparatus recited in claim 9 wherein the aerosol supply conduit subtends an angle of about 75° with the inlet of the gas conduit.

11. The apparatus recited in claim 1 wherein the aerosol supply conduit is coaxial with the inlet of the gas conduit.

12. The apparatus recited in claim 1 wherein the respiratory conduit is mounted to the connector at the outlet of the gas conduit.

13. The apparatus recited in claim 12 farther comprising an intermediate connector mounted between the respiratory conduit and the outlet of the gas conduit.

14. The apparatus recited in claim 13 wherein the intermediate connector includes a lumen extending therethrough, and a cross-sectional area of the lumen varies along a length of the lumen.

15. The apparatus recited in claim 13 wherein the intermediate connector comprises a handle for gripping the intermediate connector.

16. The apparatus recited in claim 1 wherein the respiratory conduit is moveable relative to the gas conduit.

17. The apparatus recited in claim 1 wherein the respiratory conduit is selected from the group consisting of a mouthpiece, a face mask, and an inter-tracheal tube.

18. The apparatus recited in claim 17 farther comprising an intermediate portion between the outlet of the gas conduit and respiratory conduit, the intermediate portion being moveable relative to the respiratory conduit.

19. The apparatus recited in claim 1 wherein the respiratory conduit includes a bifurcation that separates into a first arm for inhalation to the respiratory system and a second arm for exhalation from the respiratory system.

20. The apparatus recited in claim 1 further comprising a ventilator conduit for connecting the inlet of the gas conduit to a ventilator.

21. The apparatus recited in claim 20 further comprising an intermediate connector mounted between the ventilator conduit and the inlet of the gas conduit.

22. The apparatus recited in claim 21 wherein the intermediate connector has a lumen extending therethrough, and a cross-sectional area of the lumen varies along a length of the lumen.

23. The apparatus recited in claim 21 wherein the intermediate connector comprises a handle for gripping the intermediate connector.

24. The apparatus recited in claim 1 further comprising an aerosol generator housing in which the aerosol generator is housed, wherein the connector is mounted to the aerosol generator housing.

25. The apparatus recited in claim 24 further comprising:
a signal interface to receive a control signal to control operation of the aerosol generator; and
a controller to control operation of the aerosol generator, the controller being connectable to the signal interface.

26. The apparatus recited in claim 1 wherein the vibratable member is dome-shaped.

27. The apparatus recited in claim 1 wherein the plurality of apertures are sized to aerosolize the liquid medicament by ejecting droplets of liquid medicament such that about 70% or more of the droplets by weight have a size in the range between about 1 and 5 micrometers.

* * * * *